(12) United States Patent
Ratan et al.

(10) Patent No.: US 9,345,694 B2
(45) Date of Patent: May 24, 2016

(54) COMPOUNDS FOR ENHANCING ARGINASE ACTIVITY AND METHODS OF USING SAME

(75) Inventors: Rajiv R. Ratan, Scarsdale, NY (US); Marie T. Filbin, New York, NY (US)

(73) Assignees: Cornell Research Foundation, Inc., Ithaca, NY (US); The Research Foundation of the City University of New York, New York, NY (US)

(*) Notice: Subject to any disclaimer, the term of this patent is extended or adjusted under 35 U.S.C. 154(b) by 0 days.

(21) Appl. No.: 13/416,885

(22) Filed: Mar. 9, 2012

(65) Prior Publication Data

US 2013/0245070 A1    Sep. 19, 2013

Related U.S. Application Data

(63) Continuation of application No. 12/309,500, filed as application No. PCT/US2007/016335 on Jul. 18, 2007, now abandoned.

(60) Provisional application No. 60/807,661, filed on Jul. 18, 2006.

(51) Int. Cl.
| | |
|---|---|
| A61K 31/4439 | (2006.01) |
| A61K 31/05 | (2006.01) |
| A61K 31/085 | (2006.01) |
| A61K 31/122 | (2006.01) |
| A61K 31/352 | (2006.01) |
| A61K 31/4184 | (2006.01) |
| A61K 31/36 | (2006.01) |
| A61K 31/7048 | (2006.01) |

(52) U.S. Cl.
CPC ............ *A61K 31/4439* (2013.01); *A61K 31/05* (2013.01); *A61K 31/085* (2013.01); *A61K 31/122* (2013.01); *A61K 31/352* (2013.01); *A61K 31/36* (2013.01); *A61K 31/4184* (2013.01); *A61K 31/7048* (2013.01)

(58) Field of Classification Search
CPC ................. A61K 31/4439; A61K 31/7048
See application file for complete search history.

(56) References Cited

U.S. PATENT DOCUMENTS

| | | | |
|---|---|---|---|
| 3,867,531 A | 2/1975 | Shemano | |
| 4,966,918 A | 10/1990 | Watanabe et al. | |
| 6,972,195 B2 | 12/2005 | Xu | |
| 8,206,741 B2 * | 6/2012 | Plachetka | 424/472 |
| 2004/0121004 A1 * | 6/2004 | Taneja | 424/465 |
| 2006/0142241 A1 * | 6/2006 | Yoo | 514/59 |
| 2006/0276393 A1 | 12/2006 | Milburn et al. | |

FOREIGN PATENT DOCUMENTS

WO    03066595 A2    8/2003

OTHER PUBLICATIONS

Colin Howden (Am J Med. 2004; 117(5A):44S-48S.).*
Schaller et al. (Am. J. Gastroenterol. Jul. 2006; 101(7): 1655-1665).*
Badiola et al. (PLOS ONE. Mar. 2013; 8(3): e58837, pp. 1-8).*
Ishige et al., "Flavonoids Protect Neuronal Cells from Oxidative Stress by Three Distinct Mechanisms", Free Radical Biology & Medicine, vol. 30, No. 4, pp. 433-446; 2001.
Bastianetto et al., "Natural Antioxidants and Neurodegenerative Diseases", Frontiers in Bioscience, vol. 9, pp. 3447-3452; 2004.
Uwabe et al., "HU0622: A Small Molecule Promoting GAP-43 Activation and Neurotrophic Effects", Neuropharmacology, vol. 51, pp. 727-736; 2006.

* cited by examiner

*Primary Examiner* — Scott Long
(74) *Attorney, Agent, or Firm* — Hoffman & Baron, LLP

(57) ABSTRACT

The present invention relates to a method for enhancing arginase activity in a damaged or injured cell. In other aspects, the invention provides a method for treating a disorder that can be treated by enhancing arginase activity in a human in need thereof, the method comprising administering to the human an effective amount of a compound that enhances arginase activity. Such disorders include ischemia, hypoxia, neurodegenerative disease or condition, stroke or trauma of the nervous system. In yet another aspect, the invention provides methods for promoting regeneration of a neural cell in a human in need thereof.

1 Claim, 37 Drawing Sheets

Figure 1A

| Name | Chemical Formula | Structure | Reference |
|---|---|---|---|
| Pinosylvin | $C_{14}H_{12}O_2$ | 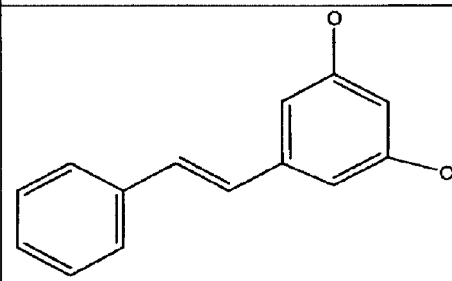 | J. Am. Chem. Soc., 1940, 62:3512 |
| Derrustone | $C_{18}H_{14}O_6$ | 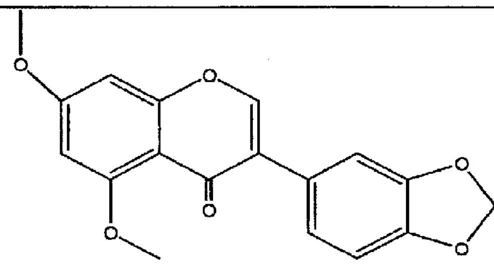 | J. Chem. Soc., 1959, 2679<br><br>Phytochemistry 1968, 7:701<br><br>Phytochemistry 1972, 11:1089 |
| Methoxyvone | $C_{17}H_{14}O_3$ | 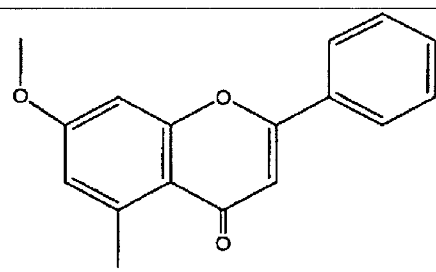 | |

Figure 1B
| Dehydrovariabilin | $C_{17}H_{14}O_4$ | 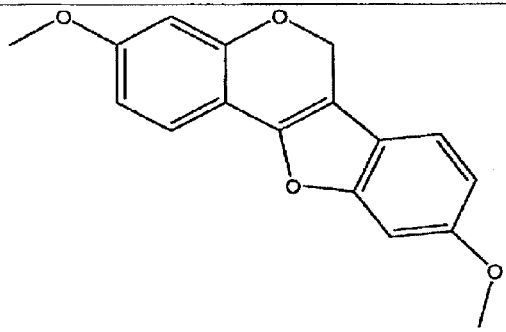 | Phytochemistry 1978, 17:1417 |
|---|---|---|---|
| Chrysophanol | $C_{15}H_{10}O_4$ | 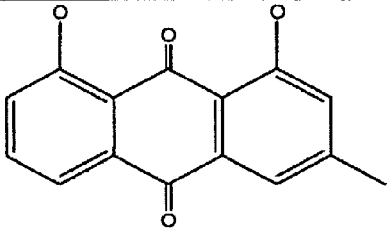 | Phytochemistry 1972, 11:2122 |

Figure 2A

| NUM | | Chem ID # | MOLENAME | Formula | Molcular Wt | cas# |
|---|---|---|---|---|---|---|
| 1 | 2-fold | 00102007 | Formononetn | C16H12O4 | 268.3 | |
| 2 | 4-fold | 00200436 | Ginkgetin | C32H22O10 | 566.5 | |
| 3 | 2-fold | 00200502 | Apigenin triacetate | C21H16O8 | 396.36 | |
| 4 | 2-fold | 00200523 | Xanthone | C13H8O2 | 196.2 | 90-47-1 |
| 5 | 2-fold | 00200789 | Daidzein | C15H10O4 | 254.2 | 456-56-8 |
| 6 | 2-fold | 00200833 | Acacetin diacetate | C20H16O7 | 368.3 | |
| 7 | 2-fold | 00200846 | Apigenin | C15H10O5 | 270.2 | |
| 8 | 2-fold | 00201066 | Pinosylvin | C14H12O2 | 212.3 | |
| 9 | 2-fold | 00201067 | Pinosylvin methyl ether | C15H14O2 | 226.3 | |
| 10 | 4-fold | 00201650 | Derrubone | C21H18O6 | 366.4 | |
| 11 | 2-fold | 00210296 | Genistein | C15H10O5 | 270.2 | |
| 12 | 4-fold | 00210454 | Robustone | C21H16O6 | 364.4 | |
| 13 | 2-fold | 00210554 | 4,7-dimethoxyflavone | C17H14O4 | 282.3 | |
| 14 | 2-fold | 00210658 | Dehydrovariabilin | C17H14O4 | 282.3 | |
| 15 | 2-fold | 00211475 | 4'-methoxychalcone | C16H14O2 | 238.3 | |
| 16 | 2-fold | 00240576 | 5,7-dimethoxyisoflavone | C17H14O4 | 282.3 | 26964-35-2 |
| 17 | 2-fold | 00240645 | Retusin 7-methyl ether | C17H14O5 | 298.3 | |
| 18 | 2-fold | 00240651 | 2-hydroxxanthone | C13H8O3 | 212.2 | |
| 19 | 2-fold | 00300384 | 5,7,4'-trimethoxyflavone | C18H16O5 | 312.3 | |

Figure 2B

| NUM | | Chem ID # | MOLENAME | Formula | Molecular Wt | cas# |
|---|---|---|---|---|---|---|
| 20 | 2-fold | 00300545 | Chrysophanol | C15H10O4 | 254.2 | |
| 21 | 2-fold | 00300601 | Biochanin a diacetate | C20H16O7 | 368.3 | |
| 22 | 2-fold | 00330007 | 3-methylcholanthrene | C21H16 | 268.4 | |
| 23 | 2-fold | 00330051 | Chlorpropham | C10H12ClNO2 | 213.7 | |
| 24 | 2-fold | 01400010 | Ipraflavone | C18H16O3 | 280.3 | |
| 25 | 2-fold | 01400666 | Methoxyvone | C17H14O3 | 266.3 | |
| 26 | 4-fold | 01401401 | Methyl robustone | C22H18O6 | 378.4 | |
| 27 | 2-fold | 01401406 | Derrushin | C19H16O7 | 356.3 | |
| 28 | 2-fold | 01401419 | Derrustone | C18H14O6 | 326.3 | |
| 29 | 2-fold | 01500351 | Indoprofen | C17H15NO3 | 281.3 | |
| 30 | 2-fold | 01500473 | Phenazopyridine hydrochloride | C11H12ClN5 | 249.7 | |
| 31 | 2-fold | 01500477 | Phenindione | C15H10O2 | 222.2 | |
| 32 | 2-fold | 01500539 | Spironolactone | C24H32O4S | 416.6 | |
| 33 | 2-fold | 01501016 | Fenbendazole | C15H13N3O2S | 299.4 | |
| 34 | 2-fold | 01502188 | Anisindione | C16H12O3 | 252.3 | |
| 35 | 4-fold | 01504044 | Resveratrol 4'-methyl ether | C15H14O3 | 242.3 | |
| 36 | 2-fold | 01504132 | 6,3'-dimethoxyflavone | C17H14O4 | 282.3 | |
| 37 | 2-fold | 01505311 | Dibenzoylmethane | C15H12O2 | 224.3 | 120-46-7 |
| 38 | 2-fold | 01505333 | Tranilast (aka MK-341) | C18H17NO5 | 327.3 | 53902-12-8 |
| 39 | 2-fold | 02300009 | Tilorone | C25H34N2O3 | 410.6 | |
| 40 | 2-fold | 10100003 | Biochanin a | C16H12O5 | 284.3 | |

Figure 3A

| Chem Name | | NUM | Well | Chem ID | Western Blot | | RT-PCR |
|---|---|---|---|---|---|---|---|
| | | | | | 1st run | 2nd run | better than control |
| Tilorone | x2 activity in primary screen | 1 | A02 | 02300009 | | | |
| Phenindione | x2 activity in primary screen | 2 | A03 | 01500477 | | | |
| Pramoxine hydrochloride | not quite 2x data in primary screens | 3 | A04 | 01501139 | | | |
| Indoprofen | x2 activity in primary screen | 4 | A05 | 01500351 | | | |
| Phenazopyridine hydrochloride | x2 activity in primary screen | 5 | A06 | 01500473 | | | |
| Piperine | not quite 2x data in primary screens | 6 | A07 | 01500873 | | | |
| 6,3'-dimethoxyflavone | x2 activity in primary screen | 7 | A08 | 01504132 | | | |
| Anisindione | x2 activity in primary screen | 8 | A09 | 01502198 | | | |
| 5,4'-dimethoxyflavone | not quite 2x data in primary screens | 9 | A10 | 00211227 | | | |
| Pinosylvin | x2 activity in primary screen | 10 | A11 | 00201066 | X | X | X |
| Derrustone | x2 activity in primary screen | 11 | B02 | 01401419 | X | X | XX |
| 4,7-dimethoxyflavone | x2 activity in primary screen | 12 | B03 | 00210554 | | | |
| Daidzein | x2 activity in primary screen | 13 | B04 | 00200789 | X | | |
| 4'-methoxychalcone | x2 activity in primary screen | 14 | B05 | 00211475 | X | | |
| Tranilast | x2 activity in primary screen | 15 | B06 | 01505333 | X | | |
| Biochanin a diacetate | x2 activity in primary screen | 16 | B07 | 00300601 | X | | |
| Resveratrol 4'-methyl | x4 activity in | 17 | B08 | 01504044 | X | | |

Figure 3B

| Chem Name | | NUM | Well | Chem ID | Western Blot | | RT-PCR |
|---|---|---|---|---|---|---|---|
| | | | | | 1st run | 2nd run | better than control |
| ether | primary screen | | | | | | |
| Derrubone | x4 activity in primary screen | 18 | B09 | 00201650 | | | |
| Chlorpropham | x2 activity in primary screen | 19 | B10 | 00330051 | | | |
| Genistein | x2 activity in primary screen | 20 | B11 | 00210296 | | | |
| Dehydrovariabilin | x2 activity in primary screen | 21 | C02 | 00210658 | X | X | X |
| Retusin 7-methyl ether | x2 activity in primary screen | 22 | C03 | 00240645 | | | |
| Xanthone | x2 activity in primary screen | 23 | C04 | 00200523 | | | |
| Pinosylvin methyl ether | x2 activity in primary screen | 24 | C05 | 00201067 | | | |
| Chrysophanol | x2 activity in primary screen | 25 | C06 | 00300545 | X | X | X |
| Apigenin | x2 activity in primary screen | 26 | C07 | 00200846 | | | |
| 2-methoxyxanthone | not quite 2x data in primary screens | 27 | C08 | 00240736 | | | |
| Apigenin triacetate | x2 activity in primary screen | 28 | C09 | 00200502 | | | |
| Fenbendazole | x2 activity in primary screen | 29 | C10 | 01501016 | | | |
| Dibenzoylmethane | x2 activity in primary screen | 30 | C11 | 01505311 | | | |
| Methoxyvone | x2 activity in primary screen | 31 | D02 | 01400666 | X | X | X |
| Ginkgetin, k salt | x4 activity in primary screen | 32 | D03 | 00200436 | | | |
| Methyl robustone | x4 activity in primary screen | 33 | D04 | 01401401 | | | |
| Liquiritigenin dimethyl ether | not quite 2x data in primary screens | 34 | D05 | 01600561 | | | |
| Derrusnin | x2 activity in primary screen | 35 | D06 | 01401406 | | | |

Figure 3C

|  |  | NUM | Well | Chem ID | Western Blot | | RT-PCR |
|---|---|---|---|---|---|---|---|
| Chem Name |  |  |  |  | 1st run | 2nd run | better than control |
| Biochanin a | x2 activity in primary screen | 36 | D07 | 10100003 |  |  |  |
| 5,7-dimethoxyisoflavone | x2 activity in primary screen | 37 | D08 | 00240576 |  |  |  |
| Formononetin | x2 activity in primary screen | 38 | D09 | 00102007 |  |  |  |
| 4'-methoxyflavone | not quite 2x data in primary screens | 39 | D10 | '00240958 |  |  |  |
| Acacetin diacetate | x2 activity in primary screen | 40 | D11 | 00200833 |  |  |  |

Figure 10

| Overcoming MAG inhibition in vitro | | |
|---|---|---|
| Post-treatment | | |
| Cmpd # | Name | Effect |
| 1 | Acetaminphen | None |
| 2 | Pinosylvin | None |
| 3 | Resveratol 4-methyl ether | None |
| 4 | Chrysophanol (low dose) | None |
| 5 | daidzein | None |
| 6 | anisomycin | Mild - none |
| 7 | methoxyvone | None |
| 8 | dehydrovariabilin | Mild |
| 9 | CAPE | None |
| 10 | fenbendazole | None |
| 11 | derrustone | None |
| 12 | Epicatechin pentaacetate | None |
|  | Lansoprazole | N/A |

Figure 13

| Overcoming MAG inhibition in vitro | | | |
|---|---|---|---|
| Cmpd # | Name | Pretreatment | Post treatment |
| 1 | Acetaminphen | None | None |
| 2 | Pinosylvin | None | None |
| 3 | Resveratol 4-methyl ether | None | None |
| 4 | Chrysophanol (low dose) | None | None |
| 5 | daidzein | Yes | None |
| 6 | methoxyvone | Yes | None |
| 7 | dehydrovariabilin | None' | None |
| 8 | Phenethyl Caffeate (CAPE) | None | None |
| 9 | fenbendazole | None | None |
| 10 | derrustone | None | None |
| 11 | Epicatechin pentaacetate | None | None |
| 12 | Lansoprazole | Yes | None |

MAG

Methoxyzone 5μM on MAG

Daidzein 20μM on MAG

Lanzoprazole 20μM on MAG

Figure 16A
| MOLENAME | Alt names | Structure |
|---|---|---|
| 2-hydroxyxanthone | 2- hydroxy- 9H-xanthen- 9- one | 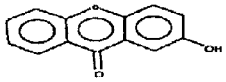 |
| 2-methoxyxanthone | 2- methoxy- 9H-xanthen- 9- one | 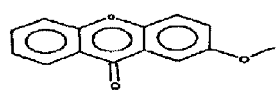 |
| 3-methylcholanthrene | 3- methyl- 1,2-dihydrocyclopenta[ij]tetraphene | 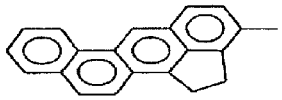 |
| 4,7-dimethoxyflavone | 7-methoxy-2-(4-methoxyphenyl)-4H-chromen-4-one (IUPAC) | 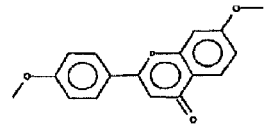 |
| 4'-methoxychalcone | (2E)-1-(4-methoxyphenyl)-3-phenylprop-2-en-1-one (IUPAC), 1-(4-methoxyphenyl)-3-phenylprop-2-en-1-one (IUPAC) | 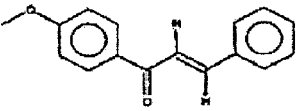 |

Figure 16B

| MOLENAME | Alt names | Structure |
|---|---|---|
| 4'-methoxyflavone | 2-(4-methoxyphenyl)-4H-chromen-4-one (IUPAC), | 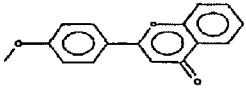 |
| 5,4'-dimethoxyflavone | 5-methoxy-2-(4-methoxyphenyl)-4H-chromen-4-one (IUPAC) | 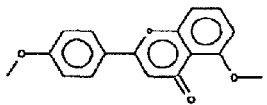 |
| 5,7,4'-trimethoxyflavone | 5,7-dimethoxy-2-(4-methoxyphenyl)-4H-chromen-4-one (IUPAC) | 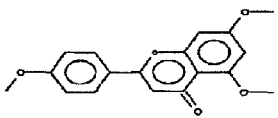 |
| 5,7-dimethoxyisoflavone | 5,7-dimethoxy-3-phenyl-4H-chromen-4-one (IUPAC) | 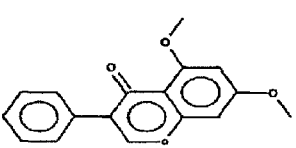 |
| 6,3'-dimethoxyflavone | 6-methoxy-2-(3-methoxyphenyl)-4H-chromen-4-one (IUPAC) | 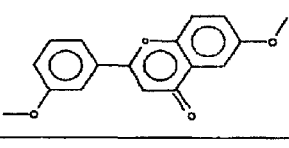 |
| Acacetin diacetate | 2-(4-methoxyphenyl)-4-oxo-4H-chromene-5,7-diyl diacetate | 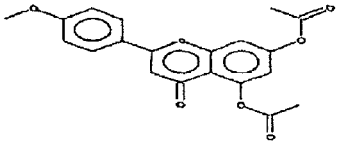 |

Figure 16C

| MOLENAME | Alt names | Structure |
|---|---|---|
| Anisindione | 2-(4-methoxyphenyl)-1H-indene-1,3(2H)-dione | 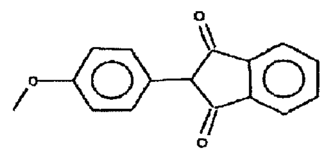 |
| Apigenin | 4',5,7-trihydroxyflavone (chemical), 4H-1-benzopyran-4-one,5,7-dihydroxy-2-(4-hydroxyphenyl)-(chemical), 5,7,4'-trihydroxy-flavone (chemical), 5,7-dihydroxy-2-(4-hydroxyphenyl)-4H-chromen-4-one (IUPAC), 83244 (NSC), apigenin (common, vendor, MeSH, primary-common), apigenine (common), apigenol (common), C.I. natural yellow 1 (common), flavone,4',5,7-trihydroxy- (chemical), NP-000448 (extract), pelargidenon 1449 (common), spigenin (common), versulin (common) | 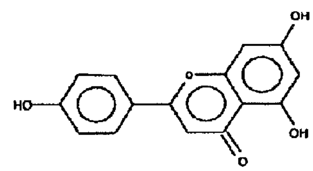 |
| Apigenin triacetate | 2-(4-acetoxyphenyl)-4-oxo-4H-chromene-5,7-diyl diacetate | 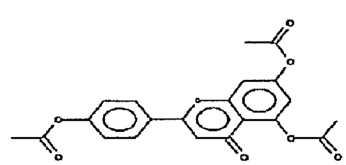 |

Figure 16D

| MOLENAME | Alt names | Structure |
|---|---|---|
| Biochanin a | 5,7- diydroxy- 3- (4-methoxyphenyl) - 4H-chromen- 4- one | 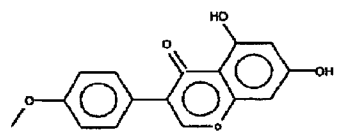 |
| Biochanin a diacetate | 3-(4-methoxyphenyl)-4-oxo-4H-chromene-5,7-diyl diacetate | 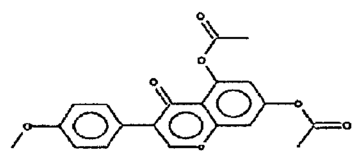 |
| Chlorpropham | isopropyl (3-chlorophenyl) carbamate | 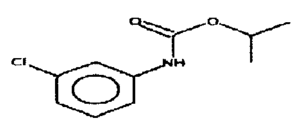 |
| Chrysophanol | 1,8-dihydroxy-3-methyl-9,10-anthraquinone | 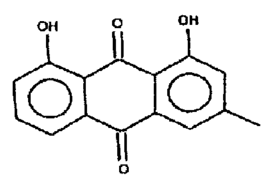 |

Figure 16E

| MOLENAME | Alt names | Structure |
|---|---|---|
| Daidzein | 4',7-dihydroxy-iso-flavone (chemical), 4',7-dihydroxyisoflavone (chemical), 4H-1-benzopyran-4-one,7-hydroxy-3-(4-hydroxyphenyl)- (chemical), 7,4'-dihydroxyisoflavone (chemical), 7-hydroxy-3-(4-hydroxyphenyl)-4-benzopyrone (chemical), 7-hydroxy-3-(4-hydroxyphenyl)-4H-1-benzopyran-4-one (chemical), 7-hydroxy-3-(4-hydroxyphenyl)-4H-chromen-4-one (IUPAC), 7-hydroxy-3-(4-hydroxyphenyl) chromen-4-one (chemical), daidzein (common, vendor, MeSH, primary-common), daidzeol (common) | 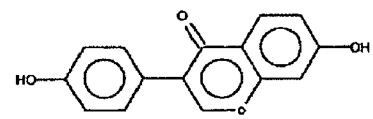 |
| Dehydrovariabilin | 3,9-dimethoxy-6H-[1]benzofuro[3,2-c]chromene | 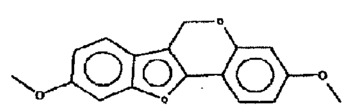 |

Figure 16F

| MOLENAME | Alt names | Structure |
|---|---|---|
| Derrubone | 3-(1,3-benzodioxol-5-yl)-5,7-dihydroxy-6-(3-methylbut-2-en-1-yl)-4H-chromen-4-one | 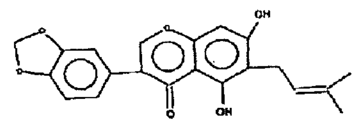 |
| Derrusnin | 3-(1,3-benzodioxol-5-yl)-4,5,7-trimethoxy-2H-chromen-2-one | 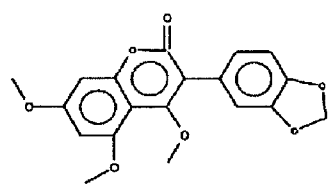 |
| Derrustone | 3-(1,3-benzodioxol-5-yl)-5,7-dimethoxy-4H-chromen-4-one | 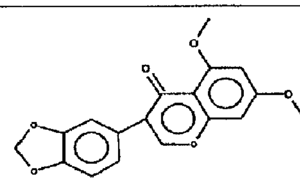 |
| Dibenzoylmethane | 1,3-diphenylpropane-1,3-dione | 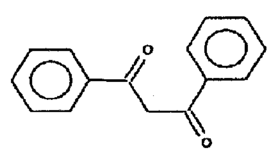 |
| Fenbendazole | methyl [6-(phenylthio)-1H-benzimidazol-2-yl]carbamate | 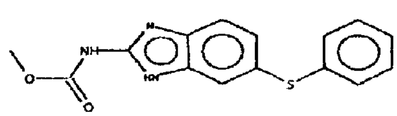 |

Figure 16G

| MOLENAME | Alt names | Structure |
|---|---|---|
| Formononetn | 7- hydroxy- 3- (4- methoxyphenyl) - 4H- chromen- 4- one | 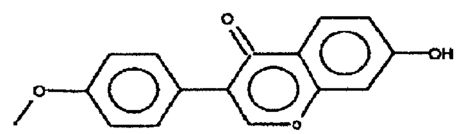 |
| Genistein | 36586 (NSC), 4',5,7-trihydroxyisoflavone (chemical), 4H-1-benzopyran-4-one,5,7-dihydroxy-3-(4-hydroxyphenyl)- (chemical), 5,7,4'-trihydroxyisoflavone (chemical), 5,7-dihydroxy-3-(4-hydroxyphenyl)-4-benzopyrone (chemical), 5,7-dihydroxy-3-(4-hydroxyphenyl)-4H-chromen-4-one (IUPAC), differenol A (common), genistein (common, MeSH, primary-common), genisteol (common), genisterin (common), isoflavone,4',5,7-trihydroxy-(chemical), NP-001561 (extract), prunetol (common), sophoricol (common) | 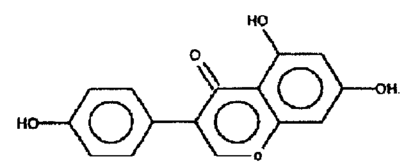 |

Figure 16H

| MOLENAME | Alt names | Structure |
|---|---|---|
| Ginkgetin | 5,7-dihydroxy-8-[5-(5-hydroxy-7-methoxy-4-oxo-4H-chromen-2-yl)-2-methoxyphenyl]-2-(4-hydroxyphenyl)-4H-chromen-4-one | 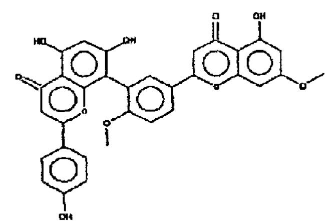 |
| Indoprofen | (2S)-2-[4-(1-oxo-1,3-dihydro-2H-isoindol-2-yl)phenyl]propanoic acid (IUPAC), 2-[4-(1-oxo-1,3-dihydro-2H-isoindol-2-yl)phenyl]propanoic acid (IUPAC) | 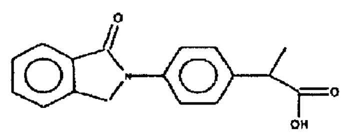 |
| Ipraflavone | 7-isopropoxy-2-phenyl-4H-chromen-4-one (IUPAC) | 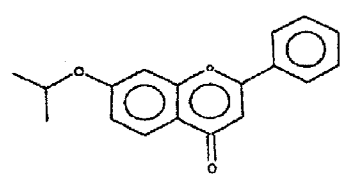 |

Figure 16I

| MOLENAME | Alt names | Structure |
|---|---|---|
| Lansoprazole (prevacid) | 2- ({[3- methyl- 4- (2,2,2- trifluoroethoxy) pyridin- 2- yl]methyl}sulfinyl) - 1H- benzimidazole (IUPAC), 2- [(S) - {[3- methyl- 4- (2,2,2- trifluoroethoxy) pyridin- 2- yl]methyl}sulfinyl]- 1H- benzimidazole (IUPAC) | 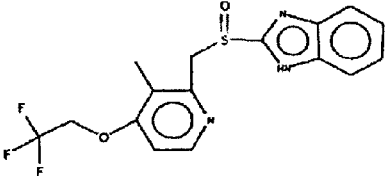 |
| Liquiritigenin dimethyl ether | (2R) - 7- methoxy- 2- (4- methoxyphenyl) - 2,3- dihydro- 4H- chromen- 4- one) (note: liquiritigenin is also called 7,4'- dihydroxyflavanone and 5-deoxyflavone | 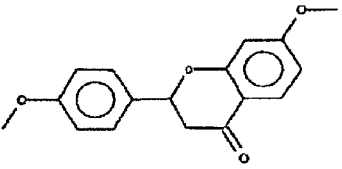 |

Figure 16J

| MOLENAME | Alt names | Structure |
|---|---|---|
| Methoxyvone | 7-methoxy-5-methyl-2-phenyl-4H-chromen-4-one | 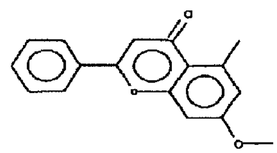 |
| Methyl robustone | 7-(1,3-benzodioxol-5-yl)-5-methoxy-2,2-dimethyl-2H,6H-pyrano[3,2-g]chromen-6-one | 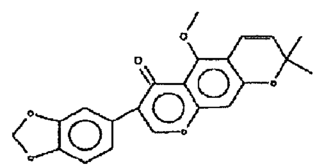 |
| Phenazopyridine hydrochloride | 3-(phenyldiazenyl)pyridine-2,6-diamine (IUPAC) | 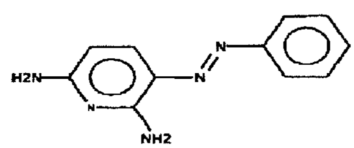 |
| Phenindione | 2-phenyl-1H-indene-1,3(2H)-dione (IUPAC) | 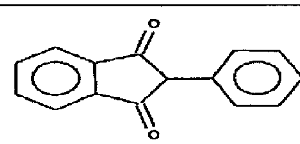 |
| Pinosylvin | 5-[(E)-2-phenylvinyl]benzene-1,3-diol (IUPAC) | 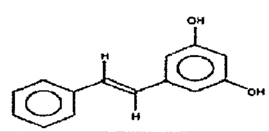 |
| Pinosylvin methyl ether | 3-methoxy-5-[(E)-2-phenylvinyl]phenol (IUPAC) | 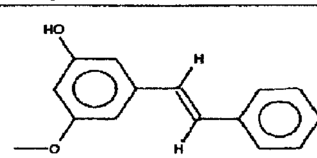 |

Figure 16K

| MOLENAME | Alt names | Structure |
|---|---|---|
| Piperine | 1-[(2E,4E)-5-(1,3-benzodioxol-5-yl)penta-2,4-dienoyl]piperidine (IUPAC), 1-[5-(1,3-benzodioxol-5-yl)penta-2,4-dienoyl]piperidine (IUPAC), | 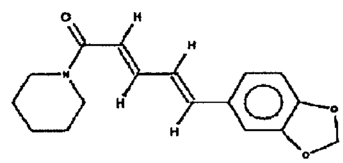 |
| Pramoxine hydrochloride | 25573 (NSC), 4-[3-(4-butoxyphenoxy)propyl]morpholine (IUPAC), | 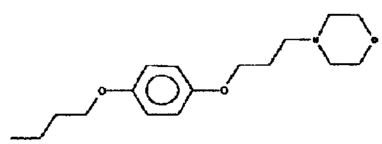 |
| Resveratrol 4'-methyl ether | 5-[(E)-2-(4-methoxyphenyl)vinyl]benzene-1,3-diol | 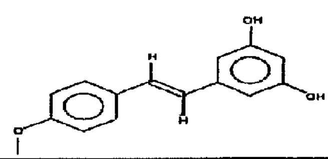 |
| Retusin 7-methyl ether | 8-hydroxy-7-methoxy-3-(4-methoxyphenyl)-4H-chromen-4-one (IUPAC) | 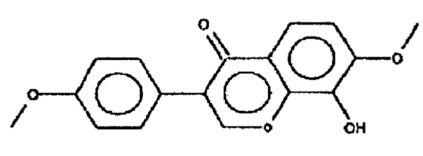 |

Figure 16L

| MOLENAME | Alt names | Structure |
|---|---|---|
| Robustone | 7-(1,3-benzodioxol-5-yl)-5-hydroxy-2,2-dimethyl-2H,6H-pyrano[3,2-g]chromen-6-one (IUPAC) | 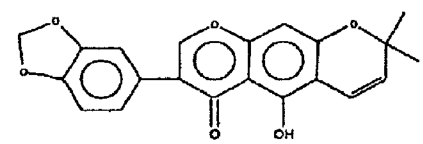 |
| Spironolactone | S-[(7R,8R,9S,10R,13S,14S,17R)-10,13-dimethyl-3,5'-dioxo-1,2,3,4',5',6,7,8,9,10,11,12,13,14,15,16-hexadecahydro-3'H-spiro[cyclopenta[a]phenanthrene-17,2'-furan]-7-yl] ethanethioate (IUPAC) | 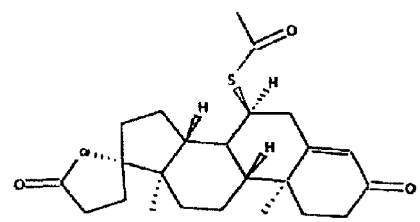 |
| Tilorone | 2,7-bis[2-(diethylamino)ethoxy]-9H-fluoren-9-one (IUPAC) | 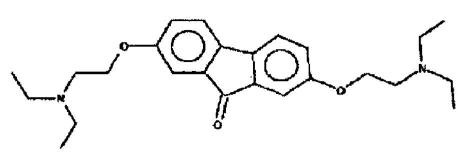 |

Figure 16M

| MOLENAME | Alt names | Structure |
|---|---|---|
| Tranilast (aka MK-341) | 2-{[(2E)-3-(3,4-dimethoxyphenyl)prop-2-enoyl]amino}benzoic acid (IUPAC) | 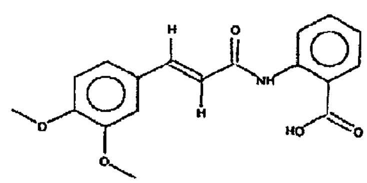 |
| Xanthone | 9H-xanthen-9-one (IUPAC) | 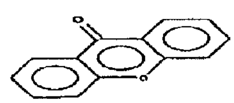 |

COMPOUNDS FOR ENHANCING ARGINASE ACTIVITY AND METHODS OF USING SAME

CROSS REFERENCE TO RELATED APPLICATIONS

This application is a continuation of U.S. Ser. No. 12/309,500, filed on Jun. 23, 2009, abandoned, which is a 371 application of PCT/US2007/016335, filed Jul. 18, 2007, which claims the benefit of U.S. Provisional Application Ser. No. 60/807,661, filed on Jul. 18, 2006. The contents of the aforementioned prior applications are incorporated herein by reference in their entireties.

The invention was made with funds from New York State Department of Health, contract number CO19772. New York State has certain rights in this invention.

BACKGROUND OF THE INVENTION

It is reported that the adult mammalian central nervous system (CNS) shows little spontaneous regeneration after injury despite that fact that there are many molecules present which promote nerve and axonal growth. In contrast to the CNS, the adult peripheral nervous system (PNS) is capable of regenerating to some extent.

It is believed that the lack of regeneration in the CNS is caused by the presence of molecules which actively prevent or inhibit regeneration. Such molecules include Nogo (an antigen of the IN-1 antibody), myelin-associated glycoprotein, and myelin-oligodendrocyte glycoprotein.

Arginase is an enzyme that catalyzes the conversion of the amino acid arginine to urea and ornithine. Arginase has been reported to reverse the inhibition of neural regeneration in the central and peripheral nervous system. Thus, enhancing arginase activity would be beneficial for reversing the inhibition of neural regeneration.

Arginase I is a 35- to 38-kDa cytoplasmic protein that cleaves arginine into urea and ornithine. Arginine is the only substrate capable of donating the guanidine group necessary for nitric oxide production. Nitric oxide is produced from arginine by three nitric oxide synthase (NOS) isoforms. Nitric oxide production can be regulated by modulating the levels of arginine. Arginase I can limit the pool of arginine available for nitric oxide synthase (NOS), thereby influencing the production of nitric oxide.

Neuronal damage can be caused by excess levels of nitric oxide (NO). NO is a diffusible neuronal second messenger synthesized in the nervous system by three enzymes: neuronal NO synthase, endothelial NO synthase, and inducible NO synthase. Excess NO generated by NO synthase is associated with various neurodegenerative diseases and conditions, such as multiple sclerosis, dementia, Huntington's disease, Alzheimer's disease, etc.

The amino acid arginine is the only endogenous substrate of NO synthase. It is reported that arginase can reduce cell death in the nervous system by competing with NO synthase for their common substrate, arginine.

Therefore, enhancing arginase activity would be beneficial for promoting neural regeneration or reducing neural damage in diseases and conditions associated with neural damage.

SUMMARY OF THE INVENTION

The present invention provides a method for enhancing arginase activity in a damaged or injured cell. The method comprises administering to a human in need thereof with an effective amount of one of the following compounds: 2-hydroxyxanthone; 2-methoxyxanthone; 3-methylcholanthrene; 4,7-dimethoxyflavone; 4'-methoxychalcone; 4'-methoxyflavone; 5,4'-dimethoxyflavone; 5,7,4'-trimethoxyflavone; 5,7-dimethoxyisoflavone; 6,3'-dimethoxyflavone; Acacetin diacetate; Anisindione; Apigenin; Apigenin triacetate; Biochanin a; Biochanin a diacetate; Chlorpropham; Chrysophanol; Daidzein; Dehydrovariabilin; Derrubone; Derrusnin; Derrustone; Dibenzoylmethane; Fenbendazole; Formononetn; Genistein; Ginkgetin; Indoprofen; Ipraflavone; Liquiritigenin dimethyl ether; Methoxyvone; Methyl robustone; Phenazopyridine hydrochloride; Phenindione; Pinosylvin; Pinosylvin methyl ether; Piperine; Pramoxine hydrochloride; Resveratrol 4'-methyl ether; Retusin 7-methyl ether; Robustone; Spironolactone; Tilorone; Tranilast; or Xanthone.

In another aspect, the invention provides a method for enhancing arginase activity in a damaged or injured cell. The method comprises administering to a human in need thereof an effective amount of Lansoprazole.

In another aspect, the invention provides a method for treating a disorder that can be treated by enhancing arginase activity in a human in need thereof. The method comprises administering to the human an effective amount of a compound that enhances arginase activity, wherein the compound is any one of the following: 2-hydroxyxanthone; 2-methoxyxanthone; 3-methylcholanthrene; 4,7-dimethoxyflavone; 4'-methoxychalcone; 4'-methoxyflavone; 5,4'-dimethoxyflavone; 5,7,4'-trimethoxyflavone; 5,7-dimethoxyisoflavone; 6,3'-dimethoxyflavone; Acacetin diacetate; Anisindione; Apigenin; Apigenin triacetate; Biochanin a; Biochanin a diacetate; Chlorpropham; Chrysophanol; Daidzein; Dehydrovariabilin; Derrubone; Derrusnin; Derrustone; Dibenzoylmethane; Fenbendazole; Formononetn; Genistein; Ginkgetin; Indoprofen; Ipraflavone; Liquiritigenin dimethyl ether; Methoxyvone; Methyl robustone; Phenazopyridine hydrochloride; Phenindione; Pinosylvin; Pinosylvin methyl ether; Piperine; Pramoxine hydrochloride; Resveratrol 4'-methyl ether; Retusin 7-methyl ether; Robustone; Spironolactone; Tilorone; Tranilast; or Xanthone.

In yet another aspect, the invention provides a method for treating a disorder that can be treated by enhancing arginase activity in a human in need thereof. The method comprises administering to the human an effective amount of Lansoprazole.

In a further aspect, the invention provides a method promoting regeneration of a neural cell in a human in need thereof. The method comprises administering to the human an effective amount of a compound that enhances arginase activity, wherein the compound is any one of the following: 2-hydroxyxanthone; 2-methoxyxanthone; 3-methylcholanthrene; 4,7-dimethoxyflavone; 4'-methoxychalcone; 4'-methoxyflavone; 5,4'-dimethoxyflavone; 5,7,4'-trimethoxyflavone; 5,7-dimethoxyisoflavone; 6,3'-dimethoxyflavone; Acacetin diacetate; Anisindione; Apigenin; Apigenin triacetate; Biochanin a; Biochanin a diacetate; Chlorpropham; Chrysophanol; Daidzein; Dehydrovariabilin; Derrubone; Derrusnin; Derrustone; Dibenzoylmethane; Fenbendazole; Formononetn; Genistein; Ginkgetin; Indoprofen; Ipraflavone; Liquiritigenin dimethyl ether; Methoxyvone; Methyl robustone; Phenazopyridine hydrochloride; Phenindione; Pinosylvin; Pinosylvin methyl ether; Piperine; Pramoxine hydrochloride; Resveratrol 4'-methyl ether; Retusin 7-methyl ether; Robustone; Spironolactone; Tilorone; Tranilast; or Xanthone.

In yet a further aspect, the invention provides a method for promoting regeneration of a neural cell in a human in need thereof. The method comprises administering to the human an effective amount of Lansoprazole.

BRIEF DESCRIPTION OF THE FIGURES

FIG. 1A. Chemical structures of compounds pinosylvin, derrustone and methoxyvone.

FIG. 1B. Chemical structures of compounds dehydrovariabilin and chrysophanol.

FIG. 2A. Table listing compounds that upregulated arginase I at least above or near 2-fold.

FIG. 2B. Table listing compounds that upregulated arginase I at least above or near 2-fold.

FIG. 3A. Table listing compounds that were tested in quantitative RT-PCR and immunoblot analysis.

FIG. 3B. Table listing compounds that were tested in quantitative RT-PCR and immunoblot analysis.

FIG. 3C. Table listing compounds that were tested in quantitative RT-PCR and immunoblot analysis.

FIG. 10. Table summarizing results of compounds tested for their ability to overcome myelin-associated glycoprotein (MAG) inhibition in P7 rat cerebellar neurons, as compared with rho kinase inhibitor. The compounds were administered after (post-treatment) the neurons were plated.

FIG. 13. Table summarizing results of compounds tested for their ability to overcome myelin-associated glycoprotein (MAG) inhibition in P7 rat cerebellar neurons, as compared with rho kinase inhibitor. The compounds were administered before (pretreatment) and after (post treatment) the neurons were plated.

FIG. 16A. The chemical formula, structures, and references for a genus of compounds useful in the methods of the invention.

FIG. 16B. The chemical formula, structures, and references for a genus of compounds useful in the methods of the invention.

FIG. 16C. The chemical formula, structures, and references for a genus of compounds useful in the methods of the invention.

FIG. 16D. The chemical formula, structures, and references for a genus of compounds useful in the methods of the invention.

FIG. 16E. The chemical formula, structures, and references for a genus of compounds useful in the methods of the invention.

FIG. 16F. The chemical formula, structures, and references for a genus of compounds useful in the methods of the invention.

FIG. 16G. The chemical formula, structures, and references for a genus of compounds useful in the methods of the invention.

FIG. 16H. The chemical formula, structures, and references for a genus of compounds useful in the methods of the invention.

FIG. 16I. The chemical formula, structures, and references for a genus of compounds useful in the methods of the invention.

FIG. 16J. The chemical formula, structures, and references for a genus of compounds useful in the methods of the invention.

FIG. 16K. The chemical formula, structures, and references for a genus of compounds useful in the methods of the invention.

FIG. 16L. The chemical formula, structures, and references for a genus of compounds useful in the methods of the invention.

FIG. 16M. The chemical formula, structures, and references for a genus of compounds useful in the methods of the invention.

DETAILED DESCRIPTION OF THE INVENTION

Method for Enhancing Arginase Activity

Figure 4:
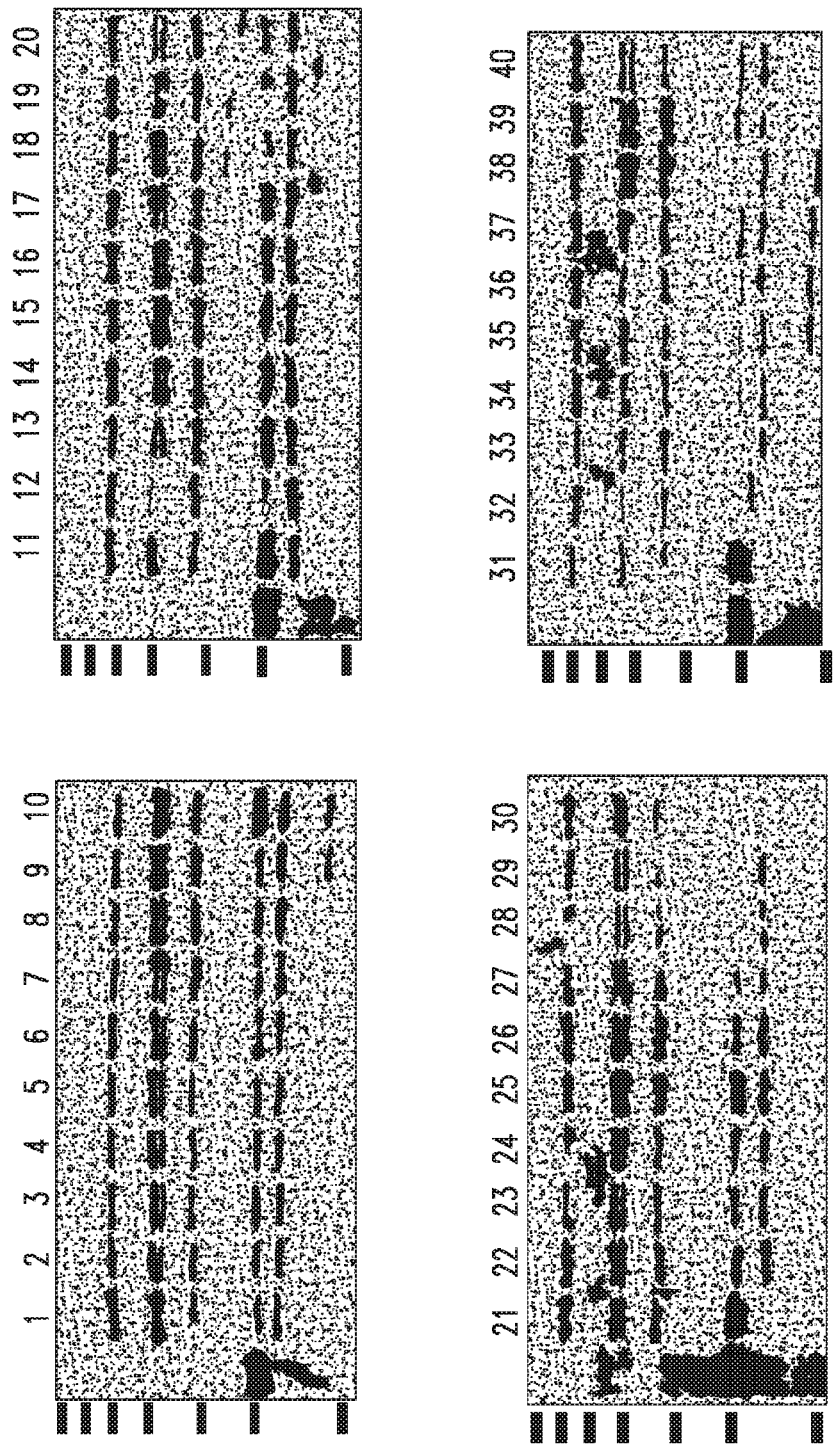
FIG. 4. Western blot results that measured level of enhanced arginase 1 protein associated with the compounds listed in FIG. 3.

In one aspect, the invention provides a method for enhancing arginase activity in a damaged or injured cell in a human in need thereof. Any isoform of arginase can be enhanced by the methods of the present invention. Examples of arginase isoforms include arginase I and arginase II.

The method comprises administering to the human an effective amount of a member of the genus of compounds selected from: 2-hydroxyxanthone; 2-methoxyxanthone; 3-methylcholanthrene; 4,7-dimethoxyflavone; 4'-methoxychalcone; 4'-methoxyflavone; 5,4'-dimethoxyflavone; 5,7,4'-trimethoxyflavone; 5,7-dimethoxyisoflavone; 6,3'-dimethoxyflavone; Acacetin diacetate; Anisindione; Apigenin; Apigenin triacetate; Biochanin a; Biochanin a diacetate; Chlorpropham; Chrysophanol; Daidzein; Dehydrovariabilin; Derrubone; Derrusnin; Derrustone; Dibenzoylmethane; Fenbendazole; Formononetn; Genistein; Ginkgetin; Indoprofen; Ipraflavone; Liquiritigenin dimethyl ether; Methoxyvone; Methyl robustone; Phenazopyridine hydrochloride; Phenindione; Pinosylvin; Pinosylvin methyl ether; Piperine; Pramoxine hydrochloride; Resveratrol 4'-methyl ether; Retusin 7-methyl ether; Robustone; Spironolactone; Tilorone; Tranilast; or Xanthone.

The terms "enhancing arginase activity" or "enhanced arginase activity" refer to an increased level of measurable arginase activity in a given assay in the presence of a candidate compound relative to the measurable level of arginase activity in the absence of the candidate compound, when tested under the same conditions.

Activity is considered enhanced according to the invention if it is enhanced at least about 10% greater, preferably at least about 25% greater, more preferably at least about 50% greater, even more preferably at least about 75% greater, most preferably at least about 90% greater, or more than in the absence of the candidate compound.

Arginase activity as used herein can be enhanced by any mechanism. For example, arginase activity could be enhanced by transcriptional induction of its cognate messenger RNA (mRNA), increased stability of its mRNA, increased translation of mRNA into protein, increased stability of arginase protein, increased arginase activity (in the presence or absence of increased protein), or any other mechanism. Increases in arginase activity could be realized by the ability of a compound to increase the affinity of the arginase enzyme for its prototypical substrate, arginine.

The arginase activity is enhanced in any damaged or injured cell that benefits from enhanced arginase or from a reduction of nitric oxide or arginine. The damage or injury may be to any part of a cell, such as to membranes, DNA, RNA, and ribosomes.

Examples of cells that may be damaged or injured include cells of the central nervous system (CNS) or peripheral nervous system (PNS), including neurons, ganglia, Schwann cells, astrocytes, oligodendrocytes, microglia cells, endothelial cells, immune cells (e.g., macrophages, T cells, B cells, and neutrophils), etc. In one embodiment, the damaged or injured cell is in a human.

In one embodiment, the method comprises administering to a human in need thereof an effective amount of any one or any combination of the following compounds: Pinosylvin; Derrustone; Methoxyvone; Dehydrovariabilin; or Chrysophanol.

In another embodiment, the method comprises administering to a human in need thereof an effective amount of any one or any combination of the following compounds: Resveratrol 4'-methyl ether; Derrubone; Ginkgetin; or Methyl robustone.

In yet another embodiment, the method comprises administering to a human in need thereof an effective amount of any one or any combination of the following compounds: Tilorone; Phenindione; Pramoxine hydrochloride; Indoprofen; Phenazopyridine hydrochloride; Piperine; 6,3'-dimethoxyflavone; Anisindione; 5,4'-dimethoxyflavone; Pinosylvin; Derrustone; 4,7-dimethoxyflavone; Daidzein; 4'-methoxychalcone; Tranilast; Biochanin a diacetate; Resveratrol 4'-methyl ether; Derrubone; Chlorpropham; Genistein; Dehydrovariabilin; Retusin 7-methyl ether; Xanthone; Pinosylvin methyl ether; Chrysophanol; Apigenin; 2-methoxyxanthone; Apigenin triacetate; Fenbendazole; Dibenzoylmethane; Methoxyvone; Ginkgetin, k salt; Methyl robustone; Liquiritigenin dimethyl ether; Derrusnin; Biochanin a; 5,7-dimethoxyisoflavone; Formononetin; 4'-methoxyflavone; or Acacetin diacetate.

In a further embodiment, the method comprises administering to a human in need thereof an effective amount of any one or any combination of the following compounds: Pinosylvin; Derrustone; Daidzein; 4'-methoxychalcone; Tranilast; Biochanin a diacetate; Resveratrol 4'-methyl ether; Dehydrovariabilin; Chrysophanol; or Methoxyvone.

In yet a further embodiment, the method comprises administering to a human in need thereof an effective amount of any one or any combination of the following compounds: Daidzein or Methoxyvone.

In another embodiment, the method comprises administering to a human in need thereof an effective amount of a compound comprising a 9H-xanthen-9-one selected from a group consisting of: 2-hydroxyxanthone, 2-methoxyxanthone, and Xanthone.

In yet another embodiment, the method comprises administering to a human in need thereof an effective amount of a compound comprising a 4H-chromen-4-one selected from a group consisting of: 4,7-dimethoxyflavone; 4'-methoxyflavone; 5,4'-dimethoxyflavone; 5,7,4'-trimethoxyflavone; 5,7-dimethoxyisoflavone; 6,3'-dimethoxyflavone; Acacetin diacetate; Apigenin; Apigenin triacetate; Biochanin a; Biochanin a diacetate; Daidzein; Derrubone; Derrustone; Formononetn; Genistein; Ginkgetin; Ipraflavone; Liquiritigenin dimethyl ether; Methoxyvone; and Retusin 7-methyl ether.

In a further embodiment, the method comprises administering to a human in need thereof an effective amount of a compound comprising a (4-methoxyphenyl)-4H-chromene-4-one selected from a group consisting of: 4,7-dimethoxyflavone; 4'-methoxyflavone; 5,4'-dimethoxyflavone; 5,7,4'-trimethoxyflavone; Acacetin diacetate; Biochanin a; Biochanin a diacetate; Formononetn; and Retusin 7-methyl ether.

In still another embodiment, the method comprises administering to a human in need thereof a compound comprising a 1,3-benzodioxol selected from a group consisting of: Derrubone; Derrusnin; Derrustone; Methyl robustone; Piperine; and Robustone.

In yet a further embodiment, the method comprises administering to a human in need thereof an effective amount of a compound selected from any one or a combination of compounds listed in FIG. 2 and/or FIG. 3.

In another aspect of the invention, the method comprises administering to the human in need thereof an effective amount of Lansoprazole.

Method for Treating a Disorder that can be Treated by Enhancing Arginase Activity In another aspect, the invention provides a method for treating a disorder that can be treated by enhancing arginase activity in a human in need thereof. The method includes administering to the human an effective amount of a compound that enhances arginase activity, wherein the compound is any one of the following: 2-hydroxyxanthone; 2-methoxyxanthone; 3-methylcholanthrene; 4,7-dimethoxyflavone; 4'-methoxychalcone; 4'-methoxyflavone; 5,4'-dimethoxyflavone; 5,7,4'-trimethoxyflavone; 5,7-dimethoxyisoflavone; 6,3'-dimethoxyflavone; Acacetin diacetate; Anisindione; Apigenin; Apigenin triacetate; Biochanin a; Biochanin a diacetate; Chlorpropham; Chrysophanol; Daidzein; Dehydrovariabilin; Derrubone; Derrusnin; Derrustone; Dibenzoylmethane; Fenbendazole; Formononetn; Genistein; Ginkgetin; Indoprofen; Ipraflavone; Liquiritigenin dimethyl ether; Methoxyvone; Methyl robustone; Phenazopyridine hydrochloride; Phenindione; Pinosylvin; Pinosylvin methyl ether; Piperine; Pramoxine hydrochloride; Resveratrol 4'-methyl ether; Retusin 7-methyl ether; Robustone; Spironolactone; Tilorone; Tranilast; or Xanthone.

In one embodiment, the method comprises administering to the human an effective amount of any one or any combination of the following compounds: Pinosylvin; Derrustone; Methoxyvone; Dehydrovariabilin; or Chrysophanol.

In another embodiment, the method comprises administering to the human an effective amount of any one or any combination of the following compounds: Resveratrol 4'-methyl ether; Derrubone; Ginkgetin; or Methyl robustone.

In yet another embodiment, the method comprises administering to the human an effective amount of any one or any combination of the following compounds: Tilorone; Phenindione; Pramoxine hydrochloride; Indoprofen; Phenazopyridine hydrochloride; Piperine; 6,3'-dimethoxyflavone; Anisindione; 5,4'-dimethoxyflavone; Pinosylvin; Derrustone; 4,7-dimethoxyflavone; Daidzein; 4'-methoxychalcone; Tranilast; Biochanin a diacetate; Resveratrol 4'-methyl ether; Derrubone; Chlorpropham; Genistein; Dehydrovariabilin; Retusin 7-methyl ether; Xanthone; Pinosylvin methyl ether; Chrysophanol; Apigenin; 2-methoxyxanthone; Apigenin triacetate; Fenbendazole; Dibenzoylmethane; Methoxyvone; Ginkgetin, k salt; Methyl robustone; Liquiritigenin dimethyl ether; Derrusnin; Biochanin a; 5,7-dimethoxyisoflavone; Formononetn; 4'-methoxyflavone; or Acacetin diacetate.

In a further embodiment, the method comprises administering to the human an effective amount of any one or any combination of the following compounds: Pinosylvin; Derrustone; Daidzein; 4'-methoxychalcone; Tranilast; Biochanin a diacetate; Resveratrol 4'-methyl ether; Dehydrovariabilin; Chrysophanol; or Methoxyvone.

In yet a further embodiment, the method comprises administering to the human an effective amount of any one or any combination of the following compounds: Daidzein or Methoxyvone.

In another embodiment, the method comprises administering to the human an effective amount of a compound comprising a 9H-xanthen-9-one selected from a group consisting of: 2-hydroxyxanthone, 2-methoxyxanthone, and Xanthone.

In yet another embodiment, the method comprises administering to the human an effective amount of a compound comprising a 4H-chromen-4-one selected from a group consisting of: 4,7-dimethoxyflavone; 4'-methoxyflavone; 5,4'-dimethoxyflavone; 5,7,4'-trimethoxyflavone; 5,7-dimethoxyisoflavone; 6,3'-dimethoxyflavone; Acacetin diacetate; Apigenin; Apigenin triacetate; Biochanin a; Biochanin a diacetate; Daidzein; Derrubone; Derrustone; Formononetn; Genistein; Ginkgetin; Ipraflavone; Liquiritigenin dimethyl ether; Methoxyvone; and Retusin 7-methyl ether.

In a further embodiment, the method comprises administering to the human an effective amount of a compound comprising a (4-methoxyphenyl)-4H-chromene-4-one selected from a group consisting of: 4,7-dimethoxyflavone; 4'-methoxyflavone; 5,4'-dimethoxyflavone; 5,7,4'-trimethoxyflavone; Acacetin diacetate; Biochanin a; Biochanin a diacetate; Formononetn; and Retusin 7-methyl ether.

In still another embodiment, the method comprises administering to the human an effective amount of a compound comprising a 1,3-benzodioxol selected from a group consisting of: Derrubone; Derrusnin; Derrustone; Methyl robustone; Piperine; and Robustone.

In yet a further embodiment, the method comprises administering to the human an effective amount of a compound selected from any one or a combination of compounds listed in FIG. 2 and/or FIG. 3.

In another aspect of the invention, the method comprises administering to the human an effective amount of Lansoprazole.

Disorders and diseases in which enhancing arginase activity is desired for treatment include ischemia, hypoxia, neurodegenerative disease or condition, or stroke. Additional disorders and diseases in which enhancing arginase activity is desired for treatment traumatic disorders (including but not limited to spinal cord injuries, spinal cord lesions, or other CNS pathway lesions), surgical nerve lesions, damage secondary to infarction, infection, exposure to toxic agents, malignancy, paraneoplastic syndromes, or patients with various types of neurodegenerative disorders of the central nervous system.

Method for Treating Ischemia

In one embodiment, the invention provides a method for treating ischemia in a human in need thereof. The method comprises administering to the human a compound that enhances arginase activity as described above, including those compounds grouped in the various genera and subgenera.

Any mammal suffering from ischemia can be treated in accordance with the method of the present invention. Ischemia generally refers to a condition of decreased blood flow to an organ, tissue and/or cell. The decrease in blood flow can be caused by, for example, constriction (e.g., hypoxemic vasoconstriction) or obstruction (e.g., clot, atherosclerotic plaque) of a blood vessel.

Ischemia can occur in any cell, organ, and/or tissue. Examples of cells, organs, and/or tissues which can be subjected to ischemia include neuronal cells (e.g., neurons, ganglia, Schwann cells, astrocytes, oligodendrocytes and microglia), brain, spinal cord, intestinal cells, kidney cells, heart and cardiac muscle cells such as myocytes, etc.

Method for Treating Hypoxia

In yet another embodiment, the invention provides a method for treating hypoxia in a human in need thereof. The method includes administering to the human a compound that enhances arginase activity as described above, including those compounds grouped in the genera and various subgenera.

Any mammal suffering from hypoxia can be treated in accordance with the method of the present invention. Hypoxia generally refers to a lack of oxygen to cells, organs, and/or tissues. Hypoxia can be caused by, for example, ischemia, anemia and chemical modification of blood, such as carboxyhemoglobin, etc.

Hypoxia can occur in any cell, organ, and/or tissue. Examples of cells, organs, and/or tissues which can be subjected to hypoxia include neuronal cells (e.g., neurons, ganglia, Schwann cells, astrocytes, oligodendrocytes and microglia), brain, spinal cord, kidney cells, intestinal cells, heart and cardiac muscle cells such as myocytes, skin cells, etc.

Method for Treating Neurodegenerative Disease or Condition

In still another embodiment, the invention provides a method for treating a neurodegenerative disease or condition in a human in need thereof. The method includes administering to the human a compound that enhances arginase activity as described above, including those compounds grouped in the genera and various sub-genera.

A neurodegenerative disease or condition typically refers to a disorder generally characterized by gradual and progressive loss of cells, tissue and/or organ of the central or peripheral nervous system. Examples of such cells, tissues and organs include, the brain, spinal cord, neurons, ganglia, Schwann cells, astrocytes, oligodendrocytes and microglia.

Any mammal suffering from any neurodegenerative disease or condition can be treated in accordance with the method of the present invention. For example, the neurodegenerative disease or condition can be an acute condition. Acute conditions generally occur as a result of trauma to a cell, tissue and/or organ of the nervous system. The trauma can, for example, partially or completely block blood flow to the cell, tissue and/or organ. Examples of acute neurodegenerative conditions include head injury and brain injury.

Alternatively, the neurodegenerative disease or condition can be a chronic neurodegenerative condition. Examples of chronic neurodegenerative diseases and conditions include Parkinson's disease, Alzheimer's disease, Huntington's disease and Amyotrophic Lateral Sclerosis (also known as Lou Gehrig's disease).

Additional examples of neurodegenerative disorders and diseases that can be treated by the invention include but are not limited to Alexander disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, Huntington disease, HIV-associated dementia, Kennedy's disease, Krabbe disease, Lewy body dementia, Machado-Joseph disease (Spinocerebellar ataxia type 3), Multiple sclerosis, Multiple System Atrophy, Neuroborreliosis, Parkinson disease, Pelizaeus-Merzbacher Disease, Pick's disease, Primary lateral sclerosis, Prion diseases, Refsum's disease, Sandhoff disease, Schilder's disease, Schizophrenia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, and other dementias.

Method for Treating Stroke

In a further aspect, the invention provides a method for treating stroke in a human in need thereof. The method includes administering to the human a compound that enhances arginase activity as described above, including those compounds grouped in the genera and various sub-genera.

Any mammal suffering from stroke can be treated in accordance with the method of the present invention. Stroke is a type of cardiovascular disease that generally involves the interruption of blood flow to and/or within the brain. The interruption of blood flow can be due to, for example, a blockage or rupture of an artery or vessel. The blockage typically occurs from a blood clot. As a result of the interruption of blood flow, the brain does not receive sufficient amounts of blood.

Method for Treating Trauma of the CNS or PNS

In still a further embodiment, the invention provides a method for treating trauma of the central nervous system (CNS) or peripheral nervous system (PNS) in a human in need thereof. The method includes administering to the human a compound that enhances arginase activity as described above, including those compounds grouped in the genera and various sub-genera.

Any type of trauma to the nervous system may be treated by the methods of the claimed invention. As described above, trauma of the CNS or PNS include, but are not limited to, spinal cord injuries, spinal cord lesions, other CNS pathway lesions, as well as injuries to the PNS, such as injuries to a nerve or neuron of the PNS and axon damage resulting in demyelination of the PNS. Such trauma can arise from either physical injury or disease. Any mammal suffering from a trauma of the CNS or PNS can be treated in accordance with the methods of the present invention.

For example, spinal cord injury refers to any damage to the spinal cord. The damage typically results in loss of function, such as mobility or feeling. Damage to the spinal cord can occur, for example, as a result or trauma (car accident, gunshot, falls, etc.) or disease (polio, spina bifida, Friedreich's Ataxia, etc).

Any injury to the spinal cord can be treated in accordance with the method of the present invention. For example, the injury can be a complete injury to the spinal cord. Complete injury typically refers to the lack of function (e.g., no sensation and no voluntary movement) below the site of injury. Both sides of the body are usually affected.

Alternatively, the injury may be an incomplete injury to the spinal cord. An incomplete injury generally refers to some function below the site of injury. For instance, a person with an incomplete injury may be able to move one limb more than another, may be able to feel parts of the body that cannot be moved, or may have more functioning on one side of the body than the other, etc.

Method for Promoting Regeneration of a Neural Cell in a Human in Need Thereof In another aspect, the invention provides a method for promoting regeneration of a neural cell in a human in need thereof. As described in Lange, et al., *J. Nutr.* 2004 October; 134(10 Suppl):28125-28175; discussion 2818S-2819S, arginase has a role in the axonal regeneration pathway. Arginase also has neuroprotective properties. Arginase is sufficient in protecting neurons against several apoptosis-inducing stimuli. Moreover, arginase acts as a nitric oxide-independent inhibitor of neuronal apoptosis.

Several investigators have found that molecules or drugs that prevent injury in the PNS or CNS have no effect on or worse, negatively impact the ability of the nervous system to regenerate or repair. There is thus an urgent need to identify targets whose activation would provide an environment that is simultaneously instructive for neuronal protection and repair. It is proposed that such an intervention would provide greater latitude in the timing of initiation of treatment.

Arginine can be metabolized by nitric oxide synthase to produce nitric oxide. It can also be degraded by arginase to produce urea and ornithine, which in turn is a precursor for the synthesis of polyamines. These two pathways compete for arginine. Arginase thus produces polyamines at the expense of nitric oxide.

Polyamines have been implicated in neuronal growth and development, axonal regeneration after injury, and in would healing outside of the CNS. Arginase I is upregulated and polyamine synthesis increases in neurons in response to either dbCAMP or BDNF.

By producing polyamines, arginase can overcome the effects of myelin-associated glycoprotein (MAG) and myelin on neurite outgrowth. Arginase is an enzyme that mediates repair by reducing its substrates (L-arginine) and increasing its ultimate products (polyamines), respectively.

As toxic levels of nitric oxide (NO) are implicated in acute ischemic cortical injury and motor neuron loss due to absence of trophic factors, arginase can mediate neuroprotection. By producing polyamines, arginase can overcome the effects of myelin-associated glycoprotein (MAG) and myelin on neurite outgrowth. Arginase is thus a bi-functional enzyme that mediates neuroprotection or repair by reducing its substrates (L-arginine) and increasing its ultimate products (polyamines), respectively.

As used herein, the phrase "neural cell" includes nerve cells (i.e., neurons, e.g., uni-, bi-, or mulipolar neurons) and their precursors and glial cells (e.g., macroglia such as astrocytes, oligodendrocytes, ependymal cells, radial glia, Schwann cells, Satellite cells, and microglia) and their precursors. Microglia are specialized macrophages capable of phagocytosis that protect neurons of the central nervous system. The term "precursor" refers to cells which are capable of developing into a specific cell type. For example, a neural cell precursor is a cell which is capable of developing into a mature neural cell (i.e., a cell having the characteristic morphology and function of a neural cell).

Accordingly, the claimed invention provides methods for promoting regeneration of a neural cell in a human in need thereof.

The method includes administering to the human an effective amount of a compound that enhances arginase activity, wherein the compound is any one of the following: 2-hydroxyxanthone; 2-methoxyxanthone; 3-methylcholanthrene; 4,7-dimethoxyflavone; 4'-methoxychalcone; 4'-methoxyflavone; 5,4'-dimethoxyflavone; 5,7,4'-trimethoxyflavone; 5,7-dimethoxyisoflavone; 6,3'-dimethoxyflavone; Acacetin diacetate; Anisindione; Apigenin; Apigenin triacetate; Biochanin a; Biochanin a diacetate; Chlorpropham; Chrysophanol; Daidzein; Dehydrovariabilin; Derrubone; Derrusnin; Derrustone; Dibenzoylmethane; Fenbendazole; Formononetn; Genistein; Ginkgetin; Indoprofen; Ipraflavone; Liquiritigenin dimethyl ether; Methoxyvone; Methyl robustone; Phenazopyridine hydrochloride; Phenindione; Pinosylvin; Pinosylvin methyl ether; Piperine; Pramoxine hydrochloride; Resveratrol 4'-methyl ether; Retusin 7-methyl ether; Robustone; Spironolactone; Tilorone; Tranilast; or Xanthone.

In one embodiment, the method comprises administering to the human an effective amount of any one or any combination of the following compounds: Pinosylvin; Derrustone; Methoxyvone; Dehydrovariabilin; or Chrysophanol.

In another embodiment, the method comprises administering to the human an effective amount of any one or any combination of the following compounds: Resveratrol 4'-methyl ether; Derrubone; Ginkgetin; or Methyl robustone.

In yet another embodiment, the method comprises administering to the human an effective amount of any one or any combination of the following compounds: Tilorone; Phenindione; Pramoxine hydrochloride; Indoprofen; Phenazopyridine hydrochloride; Piperine; 6,3'-dimethoxyflavone; Anisindione; 5,4'-dimethoxyflavone; Pinosylvin; Derrustone; 4,7-dimethoxyflavone; Daidzein; 4'-methoxychalcone; Tranilast; Biochanin a diacetate; Resveratrol 4'-methyl ether; Derrubone; Chlorpropham; Genistein; Dehydrovariabilin; Retusin 7-methyl ether; Xanthone; Pinosylvin methyl ether; Chrysophanol; Apigenin; 2-methoxyxanthone; Apigenin triacetate; Fenbendazole; Dibenzoylmethane; Methoxyvone; Ginkgetin, k salt; Methyl robustone; Liquiritigenin dimethyl ether; Derrusnin; Biochanin a; 5,7-dimethoxyisoflavone; Formononetin; 4'-methoxyflavone; or Acacetin diacetate.

In a further embodiment, the method comprises administering to the human an effective amount of any one or any combination of the following compounds: Pinosylvin; Derrustone; Daidzein; 4'-methoxychalcone; Tranilast; Biochanin a diacetate; Resveratrol 4'-methyl ether; Dehydrovariabilin; Chrysophanol; or Methoxyvone.

In yet a further embodiment, the method comprises administering to the human a an effective amount of n effective amount of any one or any combination of the following compounds: Daidzein or Methoxyvone.

In another embodiment, the method comprises administering to the human an effective amount of a compound comprising a 9H-xanthen-9-one selected from a group consisting of: 2-hydroxyxanthone, 2-methoxyxanthone, and Xanthone.

In yet another embodiment, the method comprises administering to the human an effective amount of a compound comprising a 4H-chromen-4-one selected from a group consisting of: 4,7-dimethoxyflavone; 4'-methoxyflavone; 5,4'-dimethoxyflavone; 5,7,4'-trimethoxyflavone; 5,7-dimethoxyisoflavone; 6,3'-dimethoxyflavone; Acacetin diacetate; Apigenin; Apigenin triacetate; Biochanin a; Biochanin a diacetate; Daidzein; Derrubone; Derrustone; Formononetn; Genistein; Ginkgetin; Ipraflavone; Liquiritigenin dimethyl ether; Methoxyvone; and Retusin 7-methyl ether.

In a further embodiment, the method comprises administering to the human an effective amount of a compound comprising a (4-methoxyphenyl)-4H-chromene-4-one selected from a group consisting of: 4,7-dimethoxyflavone; 4'-methoxyflavone; 5,4'-dimethoxyflavone; 5,7,4'-trimethoxyflavone; Acacetin diacetate; Biochanin a; Biochanin a diacetate; Formononetn; and Retusin 7-methyl ether.

In still another embodiment, the method comprises administering to the human an effective amount of a compound comprising a 1,3-benzodioxol selected from a group consisting of: Derrubone; Derrusnin; Derrustone; Methyl robustone; Piperine; and Robustone.

In yet a further embodiment, the method comprises administering to the human an effective amount of a compound selected from any one or a combination of compounds listed in FIG. 2 and/or FIG. 3.

In another aspect of the invention, the method comprises administering to the human an effective amount of Lansoprazole.

Methods for Protecting a Neural Cell in a Human in Need Thereof

In yet another aspect, the invention provides a method for protecting a neural cell in a human in need thereof. The method includes administering to the human a compound that enhances arginase activity, wherein the compound comprises any one of the following compounds: 2-hydroxyxanthone; 2-methoxyxanthone; 3-methylcholanthrene; 4,7-dimethoxyflavone; 4'-methoxychalcone; 4'-methoxyflavone; 5,4'-dimethoxyflavone; 5,7,4'-trimethoxyflavone; 5,7-dimethoxyisoflavone; 6,3'-dimethoxyflavone; Acacetin diacetate; Anisindione; Apigenin; Apigenin triacetate; Biochanin a; Biochanin a diacetate; Chlorpropham; Chrysophanol; Daidzein; Dehydrovariabilin; Derrubone; Derrusnin; Derrustone; Dibenzoylmethane; Fenbendazole; Formononetn; Genistein; Ginkgetin; Indoprofen; Ipraflavone; Liquiritigenin dimethyl ether; Methoxyvone; Methyl robustone; Phenazopyridine hydrochloride; Phenindione; Pinosylvin; Pinosylvin methyl ether; Piperine; Pramoxine hydrochloride; Resveratrol 4'-methyl ether; Retusin 7-methyl ether; Robustone; Spironolactone; Tilorone; Tranilast; or Xanthone.

In another aspect of the invention, the method comprises administering to the human an effective amount of Lansoprazole. The method includes administering to the human any one or a combination of compounds that enhances arginase activity included in the genera and sub-genera of compounds described above.

Compounds

Compounds useful in the methods of the present invention include 2-hydroxyxanthone; 2-methoxyxanthone; 3-methylcholanthrene; 4,7-dimethoxyflavone; 4'-methoxychalcone; 4'-methoxyflavone; 5,4'-dimethoxyflavone; 5,7,4'-trimethoxyflavone; 5,7-dimethoxyisoflavone; 6,3'-dimethoxyflavone; Acacetin diacetate; Anisindione; Apigenin; Apigenin triacetate; Biochanin a; Biochanin a diacetate; Chlorpropham; Chrysophanol; Daidzein; Dehydrovariabilin; Derrubone; Derrusnin; Derrustone; Dibenzoylmethane; Fenbendazole; Formononetn; Genistein; Ginkgetin; Indoprofen; Ipraflavone; Liquiritigenin dimethyl ether; Methoxyvone; Methyl robustone; Phenazopyridine hydrochloride; Phenindione; Pinosylvin; Pinosylvin methyl ether; Piperine; Pramoxine hydrochloride; Resveratrol 4'-methyl ether; Retusin 7-methyl ether; Robustone; Spironolactone; Tilorone; Tranilast; or Xanthone.

Another compound useful in the methods of the present invention includes Lansoprazole.

Further examples compounds useful in the methods of the present invention include any one or a combination of compounds listed in FIG. 2 and/or FIG. 3.

These compounds are known in the art. The chemical formula, structures, and references for a genus of compounds described above are shown in FIG. 16.

The chemical formula, structures, and references for Pinosylvin, Derrustone, Methoxyvone, Dehydrovariabilin, and Chrysophanol are shown in FIG. 1.

The compounds can be in the form of a pharmaceutically acceptable salt. The term "pharmaceutically acceptable salt" refers to a well-tolerated, nontoxic salt prepared from any basic or acidic compound mentioned above, and an acid or base, respectively. The acids may be inorganic or organic acids of any one of the compounds mentioned above. Examples of inorganic acids include hydrochloric, hydrobromic, nitric hydroiodic, sulfuric, and phosphoric acids. Examples of organic acids include carboxylic and sulfonic acids. The radical of the organic acids may be aliphatic or aromatic. Some examples of organic acids include formic, acetic, phenylacetic, propionic, succinic, glycolic, glucuronic, maleic, furoic, glutamic, benzoic, anthranilic, salicylic, phenylacetic, mandelic, embonic (pamoic), methanesulfonic, ethanesulfonic, panthenoic, benzenesulfonic, stearic, sulfanilic, alginic, tartaric, citric, gluconic, gulonic, arylsulfonic, and galacturonic acids. Appropriate organic bases may be selected, for example, from N,N-dibenzylethylenediamine, chloroprocaine, choline, diethanolamine, ethylenediamine, meglumine (N-methylglucamine), and procaine.

Throughout this specification, parameters are defined by maximum and minimum amounts. Each minimum amount can be combined with each maximum amount to define a range.

Administration

The compounds are administered to a human. The compound is administered to the human in an amount effective in achieving its purpose. The effective amount of the compound to be administered can be readily determined by those skilled in the art during pre-clinical trials and clinical trials by methods familiar to physicians and clinicians. Typical daily doses include approximately 1 mg to 1000 mg.

Any method known to those in the art for contacting a cell, organ or tissue with a compound may be employed. Suitable methods include in vitro, ex vivo, or in vivo methods. In vitro methods typically include cultured samples. For example, a cell can be placed in a reservoir (e.g., tissue culture plate), and incubated with a compound under appropriate conditions suitable for enhancing arginase activity. Suitable incubation conditions can be readily determined by those skilled in the art.

Ex vivo methods typically include cells, organs or tissues removed from a mammal, such as a human. The cells, organs or tissues can, for example, be incubated with the compound under appropriate conditions. The contacted cells, organs or tissues are normally returned to the donor, placed in a recipient, or stored for future use. Thus, the compound is generally in a pharmaceutically acceptable carrier.

In vivo methods are typically limited to the administration of a compound, such as those described above, to a mammal, preferably a human. The compounds useful in the methods of the present invention are administered to a mammal in an amount effective in enhancing arginase activity or treating the mammal. The effective amount is determined during pre-clinical trials and clinical trials by methods familiar to physicians and clinicians.

An effective amount of a compound useful in the methods of the present invention, preferably in a pharmaceutical composition, may be administered to a mammal in need thereof by any of a number of well-known methods for administering pharmaceutical compounds. The compound may be administered systemically or locally.

For example, the compound may be administered orally, intravenously, intranasally, intramuscularly, subcutaneously, or transdermally. Other routes of administration include intracerebroventricularly or intrathecally. Intracerebroventiculatly refers to administration into the ventricular system of the brain. Intrathecally refers to administration into the space under the arachnoid membrane of the spinal cord. Thus intracerebroventricular or intrathecal administration may be preferred for those diseases and conditions which affect the organs or tissues of the central nervous system.

The compounds useful in the methods of the invention may also be administered to mammals by sustained release, as is known in the art. Sustained release administration is a method of drug delivery to achieve a certain level of the drug over a particular period of time. The level typically is measured by serum or plasma concentration.

A description of methods for delivering a compound by controlled release can be found in international PCT Application No. WO 02/083106. The PCT application is incorporated herein by reference in its entirety. Other controlled release agents are described, for example, in U.S. Pat. Nos. 5,567,439; 6,838,094; 6,863,902; and 6,905,708. The controlled release agents and methods for making them in these patents are incorporated herein by reference.

Any formulation known in the art of pharmacy is suitable for administration of the compounds useful in the methods of the present invention. For oral administration, liquid or solid formulations may be used. Some examples of formulations include tablets, gelatin capsules, pills, troches, elixirs, suspensions, syrups, wafers, chewing gum and the like. The compounds can be mixed with a suitable pharmaceutical carrier (vehicle) or excipient as understood by practitioners in the art. Examples of carriers and excipients include starch, milk, sugar, certain types of clay, gelatin, lactic acid, stearic acid or salts thereof, including magnesium or calcium stearate, talc, vegetable fats or oils, gums and glycols.

For systemic, intracerebroventricular, intrathecal, topical, intranasal, subcutaneous, or transdermal administration, formulations of the compounds useful in the methods of the present inventions may utilize conventional diluents, carriers, or excipients etc., such as those known in the art to deliver the compounds. For example, the formulations may comprise one or more of the following: a stabilizer, a surfactant, preferably a nonionic surfactant, and optionally a salt and/or a buffering agent. The compound may be delivered in the form of an aqueous solution, or in a lyophilized form.

The stabilizer may, for example, be an amino acid, such as for instance, glycine; or an oligosaccharide, such as for example, sucrose, tetralose, lactose or a dextran. Alternatively, the stabilizer may be a sugar alcohol, such as for instance, mannitol; or a combination thereof. Preferably the stabilizer or combination of stabilizers constitutes from about 0.1% to about 10% weight for weight of the compound. The surfactant is preferably a nonionic surfactant, such as a polysorbate. Some examples of suitable surfactants include Tween20, Tween80; a polyethylene glycol or a polyoxyethylene polyoxypropylene glycol, such as Pluronic F-68 at from about 0.001% (w/v) to about 10% (w/v).

The salt or buffering agent may be any salt or buffering agent, such as for example, sodium chloride, or sodium/potassium phosphate, respectively. Preferably, the buffering agent maintains the pH of the pharmaceutical composition in the range of about 5.5 to about 7.5. The salt and/or buffering agent is also useful to maintain the osmolality at a level suitable for administration to a human or an animal. Preferably the salt or buffering agent is present at a roughly isotonic concentration of about 150 mM to about 300 mM.

The formulations of the compounds useful in the methods of the present invention may additionally contain one or more conventional additive. Some examples of such additives include a solubilizer such as, for example, glycerol; an antioxidant such as for example, benzalkonium chloride (a mixture of quaternary ammonium compounds, known as "quats"), benzyl alcohol, chloretone or chlorobutanol; anaesthetic agent such as for example a morphine derivative; or an isotonic agent etc., such as described above. As a further precaution against oxidation or other spoilage, the pharmaceutical compositions may be stored under nitrogen gas in vials sealed with impermeable stoppers.

EXAMPLES

Example 1

Screening for Arginase I Upregulators

A 2000 compound library was tested to identify arginase-1 upregulators. The library tested was The Spectrum Collection™ from MicroSource Discovery System, Inc. (Groton, Conn.). The 2000 compounds in the library are primarily Food and Drug Administration (FDA)-approved compounds or natural products. An alphabetical list of the compounds is available at the MicroSource Discovery website at www.ms-discovery.com/spect.html. The compounds are supplied as 10 mM solutions in dimethyl sulfoxide (DMSO).

The library was screened using murine hippocampal HT22 cells transfected with a luciferase-arginase 1 construct on 96 well plates. Total protein was also measured to use in normalization. The luciferase assay result for each compound is normalized to protein content and is expressed as luciferase/mg protein. The fold increase was measured relative to untreated control, represented as sample #1 in each HT22 Arg plate.

Ratios of the results from the "luciferase assay" and "protein assay" were tabulated. A comparison of these normalized responses indicates amount of enhanced arginase activity. Compounds and their respective Chem ID numbers that upregulated arginase 1 above or near 2 fold were identified.

See FIG. 2. The protocol that was used to screen for the Arginase I upregulators is described in detail below.

Materials

T75 flask, Corning 430641 vented
96 well plate (for tissue culture), Mictotest Primaria, flat bottom, #35-3872
96 well plate (for chemical compound), Mictotest™ 96, flat bottom, #35-3072
Dulbecco's Phosphate Buffered Saline (1×PBS), from Gibco #14190-144
0.25% Trypsin-EDTA solution, from Sigma #T4049
DMEM (Dulbecco's Modified Eagle's Medium), from Gibco #11995-040 & #11965-092
Fetal Bovine Serum (FCS), from Gibco #10082-147
Penicillin 10,000 IU/ml & Streptomycin 10,000 ug/ml (P/S) from Cellgro #30-002-C1
Puromycin 1 mg/ml stock
10 mM stock of chemical compounds in DMSO, The Spectrum Collection™ from MicroSource Discovery System. Inc; stored at −80° C.
Lysis Reagent (5×), from Promega #E153A
Luciferase Assay Substrate, from Promega #E151A
Luciferase Assay Buffer, from Promega #E152A
LmaxII$^{384}$ from Molecular Device
70% Ethanol
96-well NUNC 236107 white plate (Luciferase Assay)
UV Plate for plate reader (Protein Assay)

Reagents

DMEM for HT22—4.8 Kb Arg-Puro

| Ingredient | Stock | Final conc. | Volume |
| --- | --- | --- | --- |
| DMEM (#11965-092) | | | 445 ml |
| FCS | | 10% | 50 ml |
| P/S | | | 3 ml |
| Puromycin | 1 mg/ml | 4 µg/ml | 2 ml |
| Total | | | 500 ml |
| Lysis Reagent (10 ml per plate) | | | |
| Lysis Reagent | 5x | 1x | 8 ml |
| ddH$_2$O | | | 32 ml |
| Total | | | 40 ml |

Day 1. Harvest Cell and Seeding

Materials:

| | | |
| --- | --- | --- |
| 12x | 96 well plates (#35-3872) | Two types of DMEM medium |
| 8x | T75 Flasks | Trypsin solution |
| 2x | Glass sterile pipette | Timer |
| Sterile pipette (25 ml, 10 ml, 5 ml) | | |
| 6x | 50 ml centrifuge tubes | |
| Repeat pipette & tips | | |

Steps
1. Remove old medium from T$_{75}$ flask by suction
2. Rinse once with 5 ml 1×PBS; discard 1×PBS
3. Add 3 ml Trypsin to treat cells and incubate at 37° C. incubator for 3 min
4. Observe under microscope to see if all cells detached
5. Stop trypsin reaction by adding 10 ml DMEM and then transfer the solution into a 50 ml centrifuge tube
6. Centrifuge at 980 rpm/4 min
7. Prepare three T75 by adding 10 ml fresh medium to each flask
8. Prepare two 50 ml centrifuge tubes by adding 30 ml fresh medium to each tube 9. Discard supernatant by suction and add 8 ml fresh DMEM into the tube to resuspend the cell pellet
10. Mix and Titrate cell suspension and add 2 ml cell suspension into three T75 flasks (total 12 ml) and 1 ml to each 50 ml centrifuge tube.
11. Use repeat pipette and sterile tips to dispense 100 µl/well to six 96-well plates (for duplicate three chemical plate) from two 50 ml centrifuge tubes
12. Repeat step 1-9 for another cell line (total is twelve 96-well plates)
13. Label all plates and $T_{75}$ flask and incubate at 37° C. incubator for 24 hours or until at least 50% confluence
14. Leave three chemical plates in 4° C. refrigerator to thaw overnight Day 2. Chemical Treatment
Materials:

| 3x 96 well plates (#35-3072) | 3x Chemical plates |
|---|---|
| Repeat pipette & tips | cAMP stock (2.5 mM) (positive control) |
| 10 µl tips (12x regular and 3x long "reach") | Medium (for HT22 Luc) |

Steps
1. Check if T75 flasks reach 50-70% confluence under microscope.
2. Thaw chemical plates at room temperature for 10 minutes
3. On a sterile 96 well plate, add 100 µl/well DMEM medium (for HT22 Luc)
4. Prepare 500 µM secondary chemical stocks by adding 5 µl original 10 mM chemical stocks to 100 µl DMEM medium (1:20)
5. Add 2 µl/well chemical to duplicate plates (column #2-11) and two cell lines (HT22 Luc and HT22Arg); the final concentration is 10 µM (1:50)
6. Treat and prepare the other two chemical plates the same way
7. Use repeat pipette to add 2 µl/well 2.5 mM cAMP stock (positive control—f.c. 50 µM DFO) to column#12 for all plates; column#1 is negative control (Blank).
8. Label and incubate at 37° C. incubator for 24 hours
9. Wrap and store two secondary stock plates at 4° C. refrigerator
10. Leave original chemical plates at basement −80° C. freezer Day 3. Lysis and Read
Materials:

| 2x | Glass sterile pipette | 1x Lysis Reagent (10 ml for each plate) |
|---|---|---|
| 12x | 96-well NUNC white plate | Luciferase Assay Substrate & Buffer |
| 12x | 96-well UV plate | (1 set per plate) |
| 10 µl tips (24x regular) | | Repeat pipette & tips |
| Timer | | |

Steps
1. After 24 hrs incubation, remove all medium by suction and add 100 µl/well 1× Lysis Reagent <not sterile>; set timer to record incubation time
2. Work on one plate at a time, leave it on shaker and then work on the second plate. Move the first plate to freezer when the second plate is done. Repeat for all plates.
3. The plates have to keep in freezer at least 15 minutes or until it's ready for next step.
4. Thaw plate at room temperature
5. Prepare Substrate solution by mixing Luciferase Assay Substrate (keep in freezer) with 10 ml Luciferase Assay Buffer (thaw at room temperature)
6. Use multiple channel pipette to transfer 10 µl/well cell lysate/supernatant to a 96-well NUNC white plate for reading with Luciferase Assay
7. Use multiple channel pipette to transfer 2.5 µl/well cell lysate/supernatant to a 96-well UV plate for reading with Protein Assay
8. Stored the plate in 4° C. refrigerator or basement freezer
9. Set up and run LmaxII$^{384}$ ATP Assay:
   <control><injector-M>
   a. Wash with 70% Ethanol
   b. Wash with ddH$_2$O
   c. Reverse to release waste
   d. Prime LmaxII$^{384}$ with Luciferase Assay Substrate Solution
   e. leave plate in the equipment
   <Wash steps need to be done once per day; Prime the machine if leave without running for a long time>
   f. Read—ATP Assay (~30 min/plate)
      <Endpoint>
      Integrate: 5 sec/Shake: 5 sec
      M-injection: volume: 100 µl
         delay: 5 sec
10. When the plate is half done, start step 6-7 for continuous reading.
11. Save and calculate data

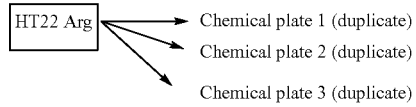

Example 2

Quantitative RT-PCR and Immunoblot Analysis

In another analysis, 40 compounds were assayed in HT22 cells on a custom plate ordered from MicroSource Discovery System, Inc. (Groton, Conn.).

FIG. 3 lists the forty compounds that were tested, along with their Microsource Discovery System, Inc. ChemID numbers, their respective plate locations, and their "compound number" for the purpose of these experiments. An "X" mark in FIG. 3 indicates whether the compound enhanced arginase activity in the respective assay.

Figure 5:
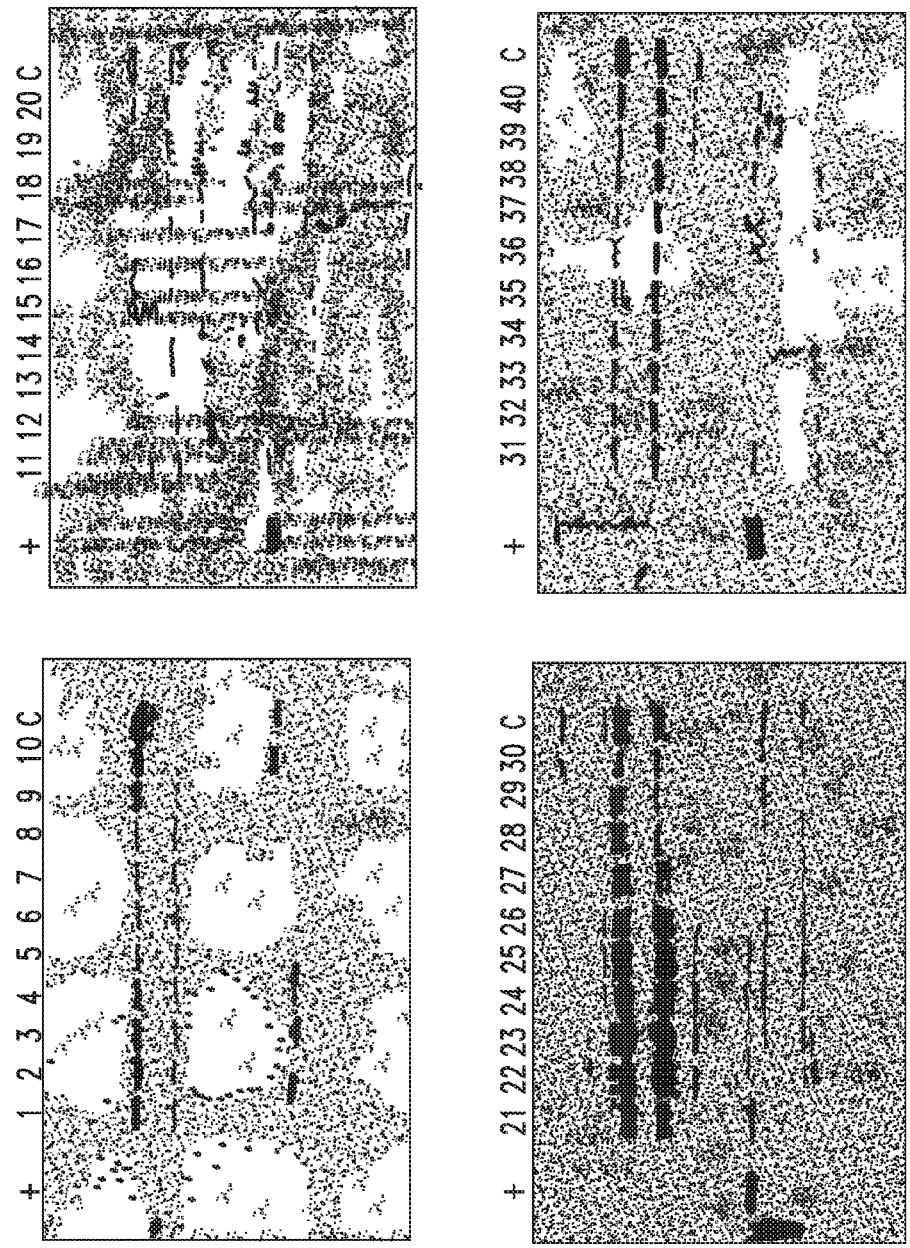
FIG. 5. Western blot results that measured level of enhanced arginase 1 protein associated with the compounds listed in FIG. 3.
Figure 6:
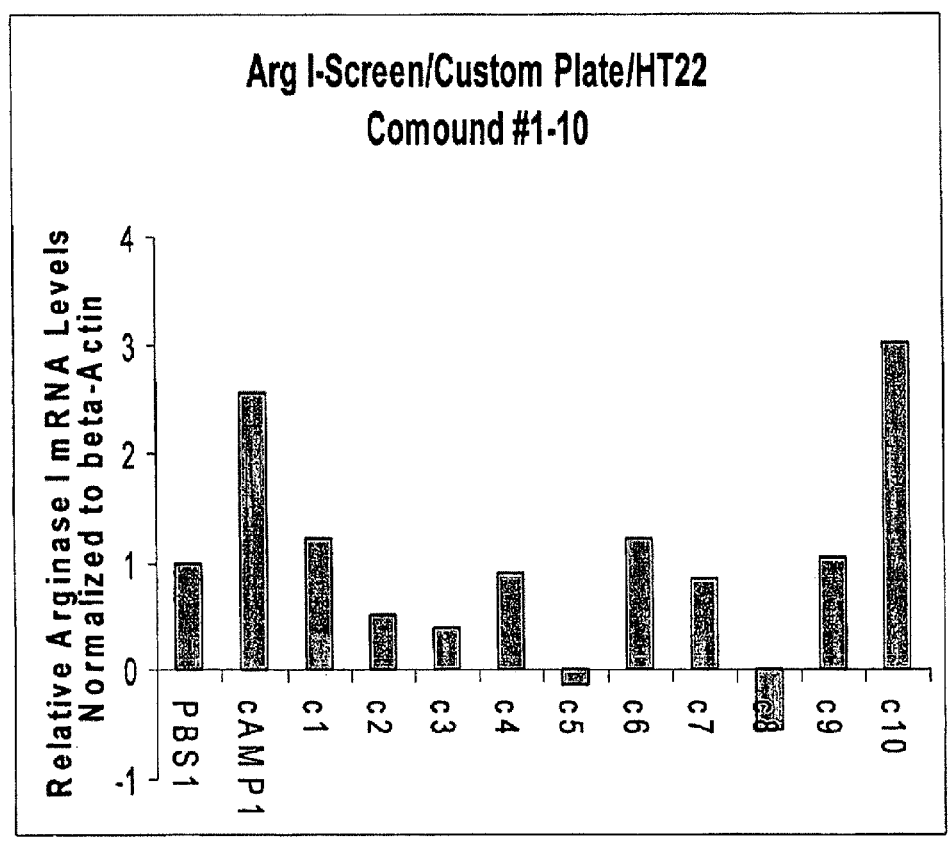
FIG. 6. Quantitative RT-PCR results presented in a graph showing levels of arginase I messenger RNA (mRNA) upregulation associated with compounds 1-10 listed in FIG. 3.
Figure 7:
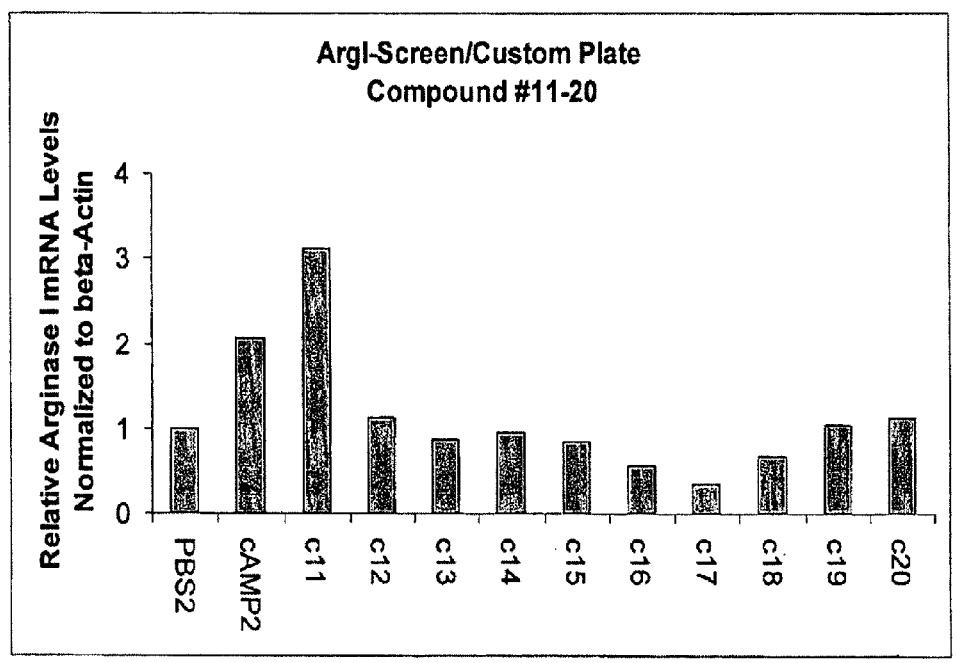
FIG. 7. Quantitative RT-PCR results presented in a graph showing levels of arginase I messenger RNA (mRNA) upregulation associated with compounds II-20 listed in FIG. 3.
Figure 8:
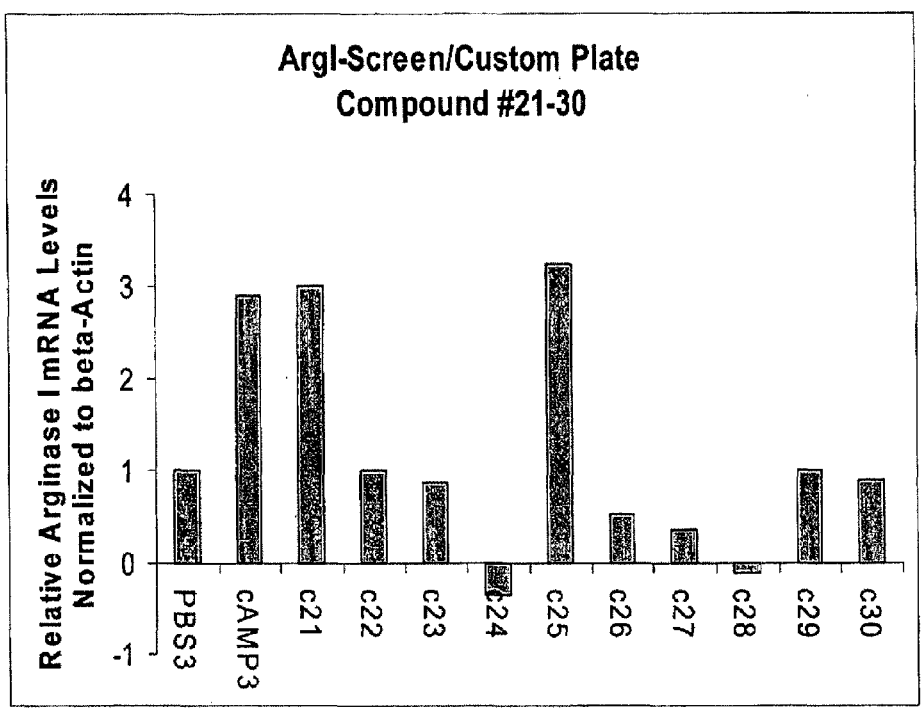
FIG. 8. Quantitative RT-PCR results presented in a graph showing levels of arginase I messenger RNA (mRNA) upregulation associated with compounds 21-30 listed in FIG. 3.
Figure 9:
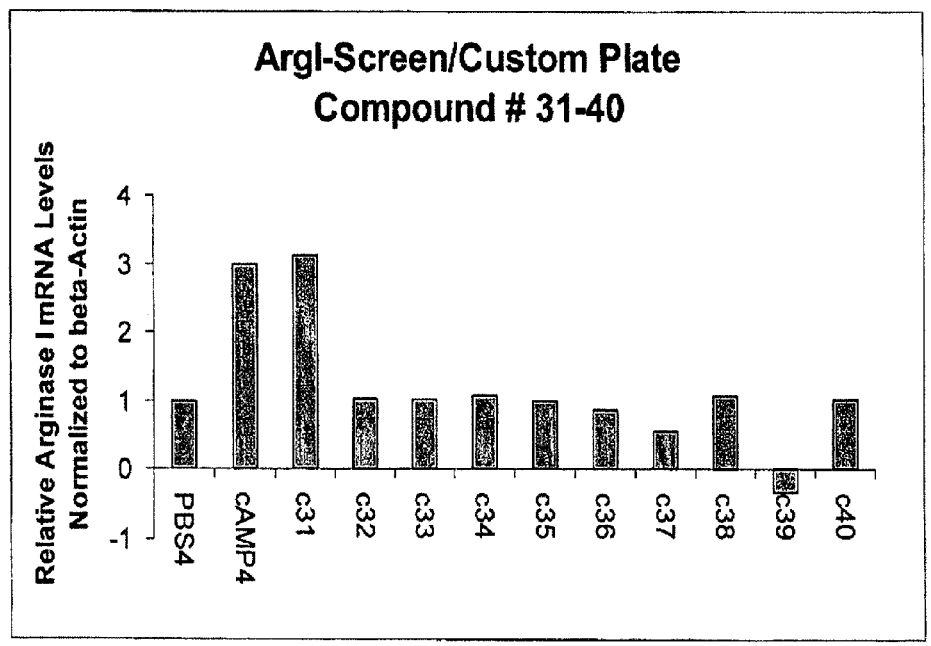
FIG. 9. Quantitative RT-PCR results presented in a graph showing levels of arginase I messenger RNA (mRNA) upregulation associated with compounds 31-40 listed in FIG. 3.

Western blots were performed to measure the level of enhanced arginase activity, i.e., arginase I expression, and mRNA levels of arginase 1. In addition, β-actin messages were measured. Western blot results were repeated, and the results of the two experiments are shown in FIGS. 4 and 5. The sample numbers listed on the top of each blot of FIGS. 4 and 5 correspond to the sample number and compound listed in FIG. 3.

In FIGS. 6 through 9, the levels of Arginase I messenger RNA (mRNA) upregulated by each of the forty compounds, normalized to β-actin, are presented. A comparison of the levels of Arginase I mRNA upregulated by each of the forty compounds normalized to β-actin indicates amount of enhanced arginase activity. Phosphate buffered saline (PBS) was used as a negative control, and cAMP was used as a positive control. The sample numbers (e.g., c1, c2) listed on the bottom of each graph of FIGS. 6 through 9 correspond to the sample number and compound listed in FIG. 3.

The protocols used for the quantitative RT-PCR and Immunoblot analyses are described in detail below.

Quantitative RT-PCR—

Total RNA was prepared from primary mixed cortical neurons using TriZOL (Invitrogen) and cDNA generating using a SuperScript III First-Strand Synthesis System for RT-PCR kit (Invitrogen), according to the manufacturer's protocol. Real time PCRs were performed as a duplex reaction using arginase gene expression assay which uses a FAM-labeled probe, and β-actin gene expression assay which uses a VIC-labeled probe (Applied Biosystems, Foster City, Calif.) so that arginase amplification could be normalized to β-actin. Real time PCRs were performed using a 7500 Real Time PCR System (Applied Biosystems) using standard PCR protocol and amplification conditions. See FIGS. 6 through 9.

Immunoblot Analysis—

Cell lysates were obtained by rinsing neurons with cold PBS followed by lysis in NP40 lysis buffer (Boston Bioproducts, Worcester, Mass.). Protein concentrations in lysates were quantified by Bradford assay (Bio-Rad, Hercules, Calif.). Nuclear and cytoplasmic protein extractions were obtained using NE-PER Nuclear and Cytoplasmic Extraction Reagents (Pierce Biotechnology, Rockford, Ill.) according to the manufacturer's protocol. Samples were boiled in Laemmli buffer and electrophoresed under reducing conditions on 12% (or 7.5% for pRb immunoblots) polyacrylamide gels. Proteins were transferred to a nitrocellulose membrane (Bio-Rad) by electroblotting. Nonspecific binding was inhibited by incubation in Tris-buffered saline with Tween 20 (TBST: 50 mM Tris-HCl, pH 8.0, 0.9% NaCl, and 0.1% Tween 20) containing 5% nonfat milk for at least 1.5 h. Primary antibodies against arginase, α-tubulin (Sigma), were diluted in TBST containing 5% milk overnight at 4° C. followed by incubation with respective horseradish peroxidase-conjugated secondary antibodies (Bio-Rad) for 2 hours at room temperature Immunoreactive proteins were detected according to the enhanced chemiluminescent protocol (Amersham Biosciences, Sunnyvale, Calif.). See FIGS. 4 and 5.

Example 3

MAG Inhibition Analysis; Comparison with Rho Kinase Inhibitor

MAG is a well-characterized protein of the central nervous system (CNS) and the peripheral nervous system (PNS). MAG has been identified as an inhibitor of axonal regeneration and neurite outgrowth. A consequence of elevated cAMP is the synthesis of polyamines, resulting from an up-regulation of Arginase I, a key enzyme in their synthesis. Inhibiting polyamine synthesis blocks the cAMP effect on regeneration. Either over-expression of Arginase I or exogenous polyamines can overcome inhibition by MAG and by myelin in general, as described by Cai, et al., Neuron. 2002 Aug. 15; 35(4):711-9.

Compounds were tested for their ability to overcome myelin-associated glycoprotein (MAG) inhibition in P7 rat cerebellar neurons.

In experiments performed in the Roman Giger laboratory at the University of Rochester School of Medicine and Dentistry, twelve compounds were tested, using the materials and methods described by Venkatesh, et al., J Neurosci. 2005 Jan. 26; 25(4):808-22. The compounds and their respective post-treatment results are listed in FIG. 10.

The twelve compounds tested were Acetaminophen; Pinosylvin; Resveratol 4-methyl ether; Chrysophanol (low dose); Daidzein; Anisomycin; Methoxyvone; Dehydrovariabilin; Phenethyl caffeate (cape); Fenbendazole; Derrustone; Epicatechin pentaacetate; Lansoprazole.

Figure 11:
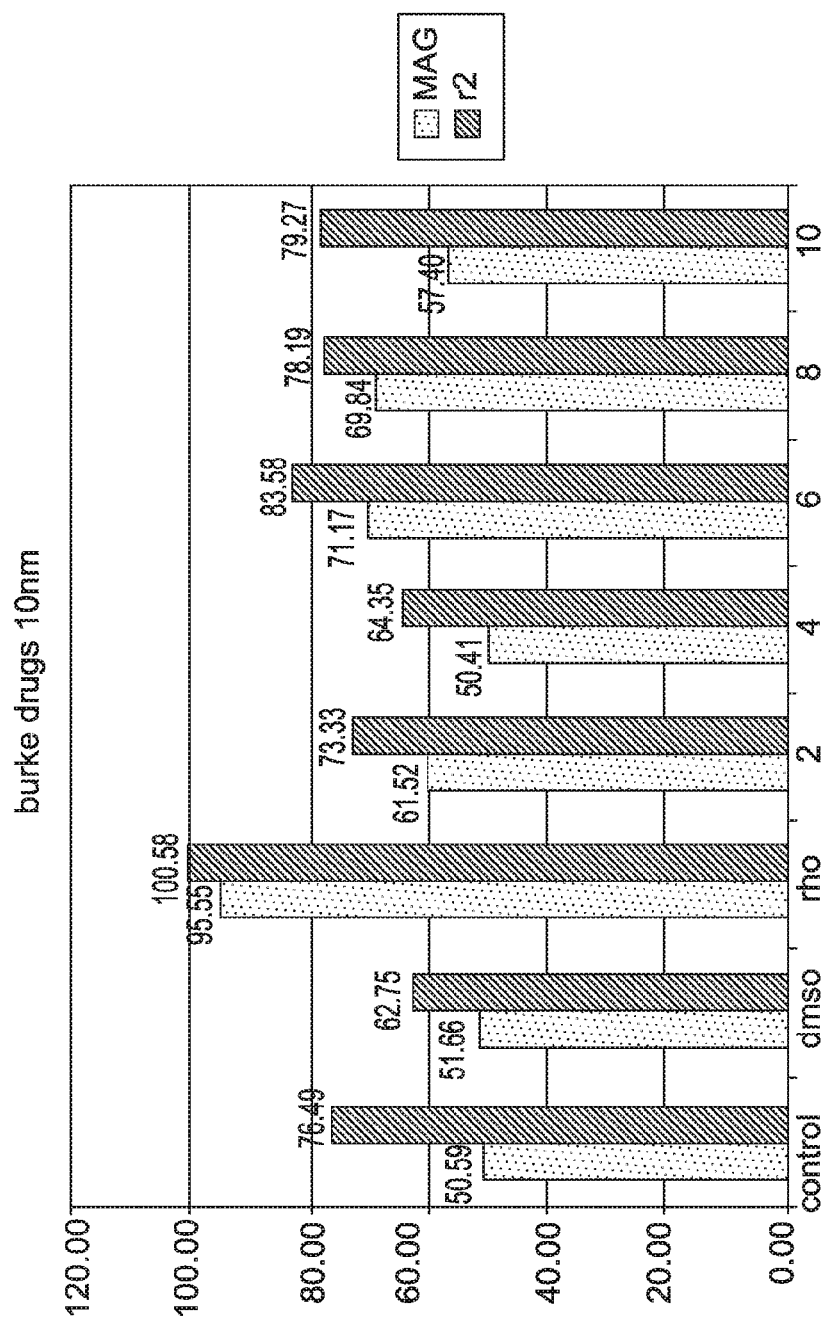
FIG. 11. Graph showing results from testing the compounds (10 nM) listed in FIG. 10 for their ability to overcome myelin-associated glycoprotein (MAG) inhibition in P7 rat cerebellar neurons, as compared with rho kinase inhibitor.
Figure 12:
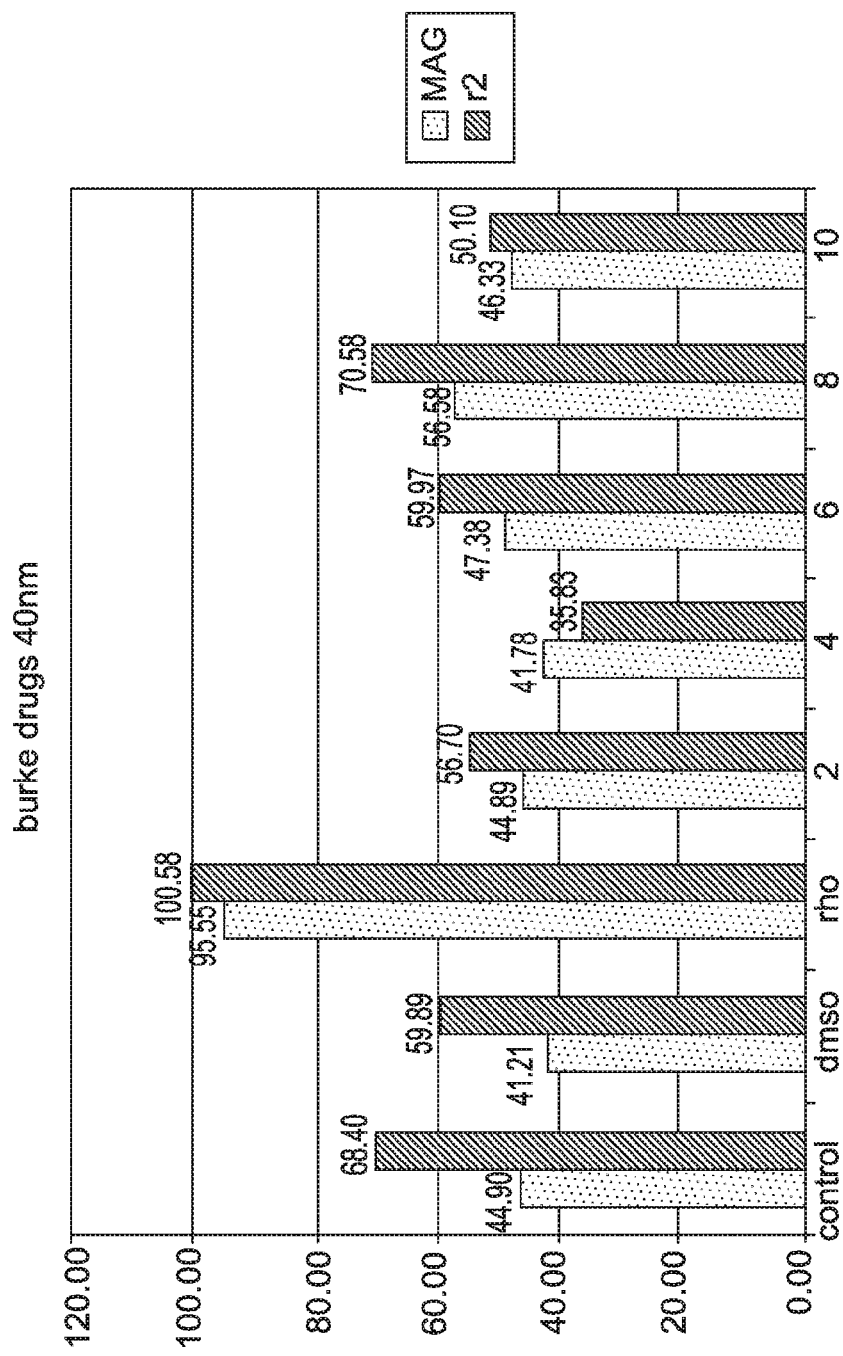
FIG. 12. Graph showing results from testing the compounds (40 nM) listed in FIG. 10 for their ability to overcome myelin-associated glycoprotein (MAG) inhibition in P7 rat cerebellar neurons, as compared with rho kinase inhibitor.
Figure 14A:
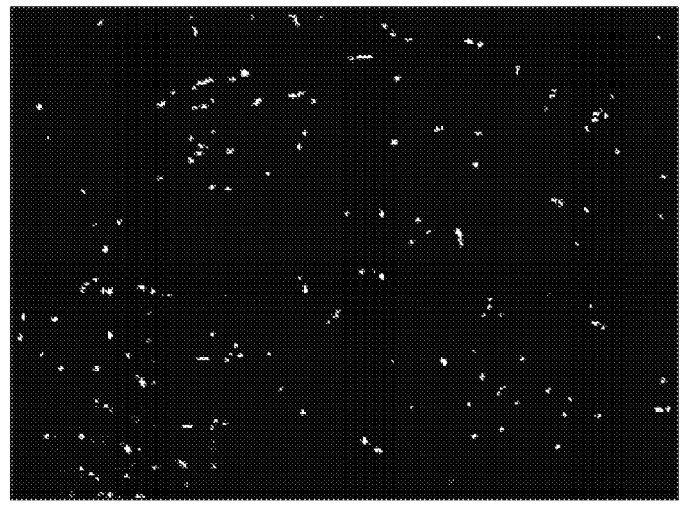
FIG. 14A. P5 cerebellar neurons were plated on CONT expressing CHO cells with DMSO (0.1%) on control CHO monolayers. Picture is representative of βIII tubulin positive cells.
Figure 14B:
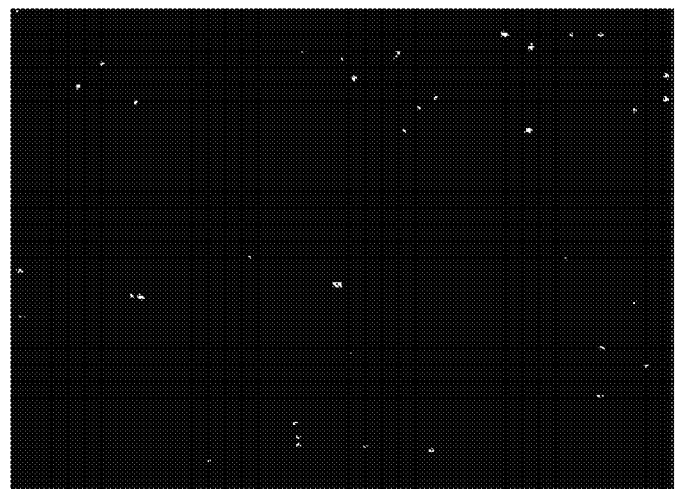
FIG. 14B. P5 cerebellar neurons were plated on substrate inhibitor MAG expressing CHO cells and treated with DMSO (0.1%). Picture is representative of βIII tubulin positive cells.
Figure 14C:
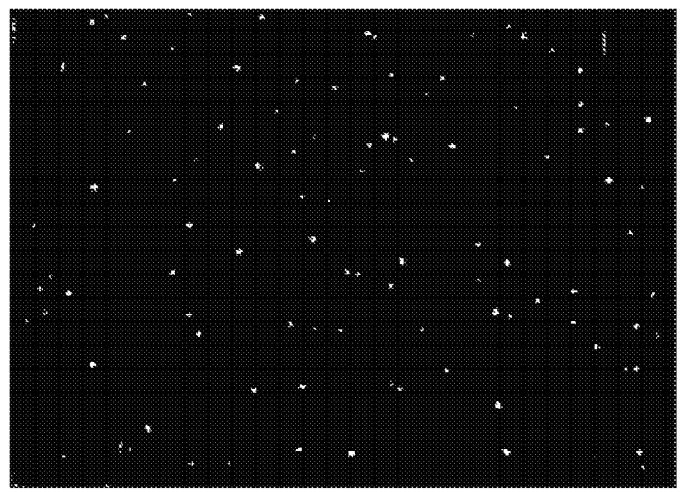
FIG. 14C. P5 cerebellar neurons were plated on substrate inhibitor MAG expressing CHO cells and treated with methoxyvone (5 μM). Picture is representative of βIII tubulin positive cells.
Figure 14D:
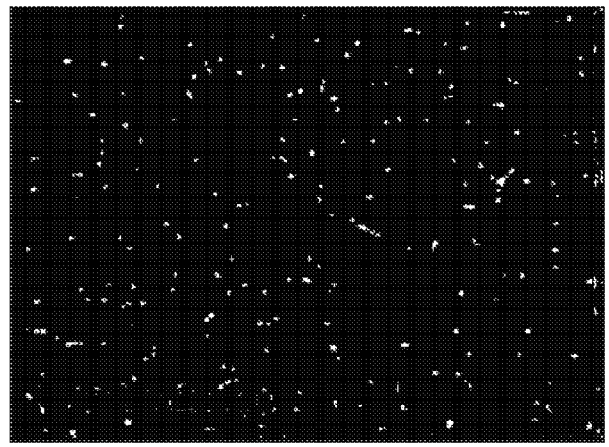
FIG. 14D. P5 cerebellar neurons were plated on substrate inhibitor MAG expressing CHO cells and treated with daidzein (20 μM). Picture is representative of βIII tubulin positive cells.
Figure 14E:
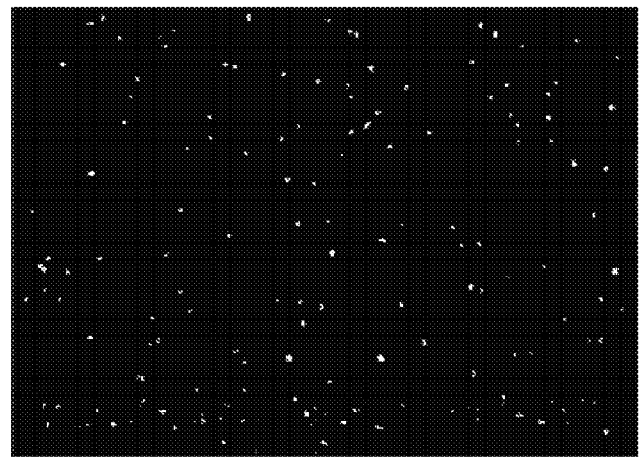
FIG. 14E. P5 cerebellar neurons were plated on substrate inhibitor MAG expressing CHO cells and treated with Lanzoprazole (20 μM). Picture is representative of βIII tubulin positive cells.
Figure 14F:
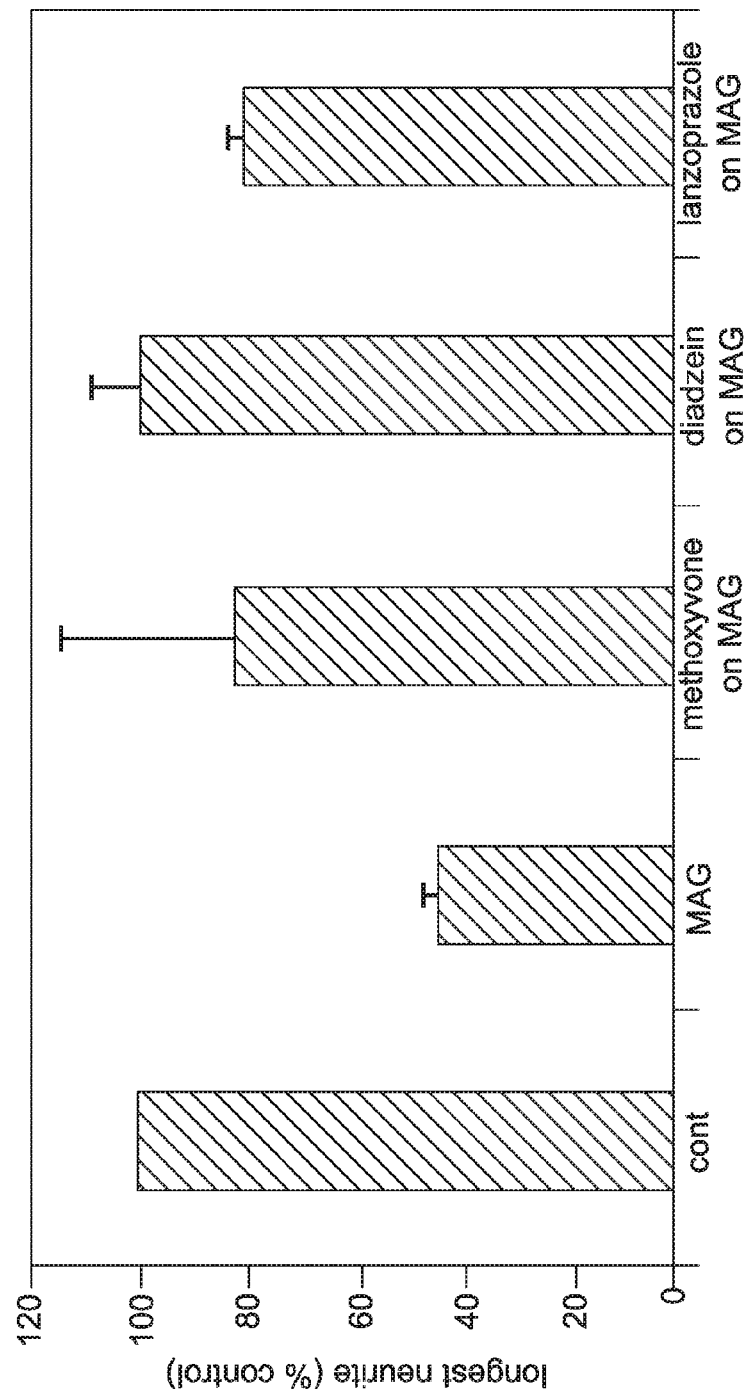
FIG. 14F. P5 cerebellar neurons were plated on CONT and substrate inhibitor (MAG) expressing CHO cells. Neurons were plated either with DMSO (0.1%) on control CHO monolayers, or on MAG and treated with DMSO (0.1%), methoxyvone (5 μM), daidzein (20 μM) and Lanzoprazole (20 μM). Graph depicts the average length of the longest neurite (percentage of the longest neurite of the control). At least 400 neurons were measured in each assay and the experiment was carried out at least twice.

The twelve compounds were tested in two different dilutions (10 nM and 40 nM final concentration). FIG. 11 shows the assay results for the compounds at 10 nM and FIG. 12 shows the assay results for the compounds at 40 nM. The compound sample numbers listed on the bottom of FIGS. 11 and 12 correspond to the compound sample numbers listed in FIG. 10.

MAG-overexpressing CHO cells and control CHO feeder layers were used in the assay. All experiments were done with Percoll purified P7 rat cerebellar neurons. The twelve compounds were tested in a "post-treatment" manner. Post-treatment refers to administering the compounds after the neurons were plated.

After 24 h in culture, cells were fixed and stained with TuJ1 (cells with neurites longer than 1 cell body diameter were quantified). Untreated cells (first column of FIGS. 11 and 12) and DMSO only (second column of FIGS. 11 and 12) were used as a negative controls. RHO-kinase inhibitor Y27632 (15 microM) (third column of FIGS. 11 and 12) was used as a positive control. All experiments have been repeated 3-5 times independently.

In FIGS. 11 and 12, there are two bars for each compound tested. One bar represents the results on the CHO-MAG cells (labeled "MAG"), and the other bar (labeled "r2") is the result on control CHO cells.

The following compounds were found to have no effect on releasing MAG inhibition: #1 (Acetaminophen), #3 (Resveratol 4-methyl ether), #5 (Daidzein), #7 (Methoxyvone), #9 CAPE, #11 (Derrustone), and #12 (epicatechin pentaacetate).

The experiment was repeated three times with the most promising compounds, which were compound #6 (Anisomycin), #8 (Dehydrovariabilin), #10 (Fenbendazole), #2 (Pinosylvin) and #4 (Chrysophanol at low doses).

Example 4

MAG Inhibition Analysis

MAG has been identified as an inhibitor of axonal regeneration and neurite outgrowth. A consequence of elevated cAMP is the synthesis of polyamines, resulting from an up-regulation of Arginase I, a key enzyme in their synthesis Inhibiting polyamine synthesis blocks the cAMP effect on regeneration. Either over-expression of Arginase I or exogenous polyamines can overcome inhibition by MAG and by myelin in general, as described by Cai, et al., Neuron. 2002 Aug. 15; 35(4):711-9.

Compounds were tested for their ability to overcome myelin-associated glycoprotein (MAG) inhibition in primary rat neurons.

Inhibiting polyamine synthesis blocks the cAMP effect on regeneration. Either over-expression of Arginase I or exogenous polyamines can overcome inhibition by MAG and by myelin in general.

In experiments performed in the Marie Filbin laboratory at Hunter College on p5 rat cerebellar neurons, twelve compounds were tested, using the materials and methods described by Mukhopadhyay, et a., Neuron. 1994 September; 13(3):757-67. The compounds and their respective post-treatment results are listed in FIG. 13.

The twelve compounds were Acetaminophen; Pinosylvin; Resveratol 4-methyl ether; Chrysophanol (low dose); Daidzein; Anisomycin; Methoxyvone; Dehydrovariabilin; Phenethyl caffeate (cape); Fenbendazole; Derrustone; Epicatechin pentaacetate; Lansoprazole. Two experiments were done.

In a first experiment, the twelve compounds were tested for their ability to overcome inhibition by MAG in culture. The compounds were tested for their ability to inhibit neurite outgrowth of MAG-expressing CHO cells. Cerebellar neurons were cultured on MAG-expressing CHO cells and neurite length is compared to neurons growing on control CHO cells, not expressing MAG.

The cells were assessed for their ability to overcome MAG inhibition when added directly to the cultures at a range of concentrations from 2-20 µM. Neurons were plated at a density of about 10,000 neurons per well of an 8-well culture dish containing a monolayer of either MAG-expressing or control CHO cells. The co-cultures were, incubated for 16-18 h and then immunostained for βIII tubulin. See FIG. 14 A-E. Neurite outgrowth was quantified as previously described (Mukhopadhyay et al., 1994). When added directly to the co-cultures, none of the compounds had any effect on inhibition by MAG. MAG inhibited neurite outgrowth as potently as when the compound was absent.

Next, the compounds were tested for their ability to overcome inhibition by MAG when the neurons were exposed to the compounds prior to being exposed to MAG—a procedure termed, "priming" Neurons were primed with the individual compounds at various concentrations ranging from 2-20 µM overnight and were then plated onto either the MAG-expressing or control CHO cell monolayers. Of the 12 compounds tested, three were able to overcome inhibition by MAG completely: Daidzein (20 µM), Lanzoprazole (20 µM) and Methoxyvone (5 µM). See FIGS. 13 and 14.

In FIG. 14, P5 cerebellar neurons were plated on CONT and MAG expressing CHO cells. See FIG. 14A-E, which are pictures representative of βIII tubulin positive cells. Neurons are plated either with DMSO (0.1%) on control CHO monolayers (FIG. 14A), or on substrate inhibitor (MAG) (FIG. 14B-E) and treated with DMSO (0.1%) (FIG. 14B), methoxyvone (5 µM) (FIG. 14C), daidzein (20 µM) and Lanzoprazole (20 µM). Graph in FIG. 14 depicts the average length of the longest neurite (percentage of the longest neurite of the control). At least 400 neurons were measured in each assay and the experiment was carried out at least twice.

The other compounds did not show as strong of an effect in overcoming MAG inhibition as the compounds Daidzein (20 µM), Lanzoprazole (20 µM) and Methoxyvone (5 µM). See FIG. 13. The overcoming of MAG inhibition occurred when the cells were "preconditioned." Preconditioning treatment means that neurons were first treated overnight with the compound and then trypsinized, plated, and allowed to grow for neurite extension for 16-18 h on the top of the CHO monolayers. Neurons that were directly treated with the different compounds on the top of the monolayers did not show any overcoming of MAG inhibition.

Figure 15:
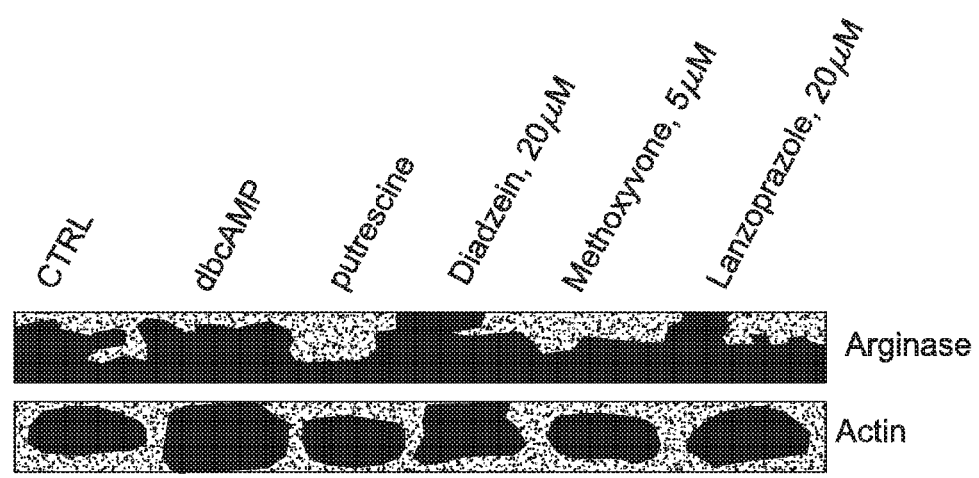
FIG. 15. Western blot and immunostaining results for arginase I protein. Neurons were treated with, daidzein (20 μM), methoxyvone (5 μM) or lanzoprazole (20 μM) for 18 hours and were then lysed and subjected to gel electrophoresis, followed by western blotting and immunostaining for Arginase I protein. As a positive control, neurons were treated with 1 mM db cAMP.

In a second experiment, the twelve compounds were tested for their ability to upregulate arginase I protein. Neurons were treated with, daidzein (20 µM), methoxyvone (5 µM) or lanzoprazole (20 µM) for 18 hours and were then lysed and subjected to gel electrophoresis, followed by western blotting and immunostaining for Arginase I protein. See FIG. 15. As a positive control, neurons were treated with 1 mM db cAMP (FIG. 15). Db-cAMP was previously shown to increased Arginase I protein 3-fold as described by Cai, et a., *Neuron*. 2002 Aug. 15; 35(4):711-9.

As was shown previously (Cai et al., 2002), Arginase I is up-regulated in response to treatment with dbcAMP. As shown presently, Arginase I protein level is also up-regulated after the treatment with daidzein (20 µM), methoxyvone (5 µM) or Lanzoprazole (20 µM).

What is claimed is:

1. A method for treating a disorder that can be treated by enhancing arginase activity in a human in need thereof, the method consisting of administering to the human an effective amount of Lansoprazole, or a pharmaceutically acceptable salt of such compound, and a carrier and/or excipient, wherein the disorder is stroke.

* * * * *